US007935495B2

(12) United States Patent
McDonald et al.

(10) Patent No.: US 7,935,495 B2
(45) Date of Patent: May 3, 2011

(54) METHODS OF DETECTING EARLY RENAL DISEASE IN ANIMALS

(75) Inventors: Thomas McDonald, Omaha, NE (US); Wayne Arthur Jensen, Wellington, CO (US); Annika Weber, Omaha, NE (US); Janet S. Andrews, Fort Collins, CO (US)

(73) Assignee: Heska Corporation, Loveland, CO (US)

( * ) Notice: Subject to any disclaimer, the term of this patent is extended or adjusted under 35 U.S.C. 154(b) by 1133 days.

(21) Appl. No.: 11/627,784

(22) Filed: Jan. 26, 2007

(65) Prior Publication Data

US 2009/0098583 A1    Apr. 16, 2009

Related U.S. Application Data

(62) Division of application No. 10/112,648, filed on Mar. 28, 2002, now Pat. No. 7,172,873.

(60) Provisional application No. 60/342,268, filed on Dec. 21, 2001, provisional application No. 60/279,391, filed on Mar. 28, 2001.

(51) Int. Cl.
*G01N 31/00* (2006.01)
*G01N 33/53* (2006.01)

(52) U.S. Cl. ........... 435/7.21; 435/7.1; 436/1; 436/501; 436/518; 424/9.1; 424/520; 422/1; 422/50; 530/300; 530/350

(58) Field of Classification Search .................. None
See application file for complete search history.

(56) References Cited

U.S. PATENT DOCUMENTS

| | | | |
|---|---|---|---|
| 4,163,778 | A | 8/1979 | Ohman et al. |
| 4,281,061 | A | 7/1981 | Zuk et al. |
| 4,659,678 | A | 4/1987 | Forrest et al. |
| 4,804,625 | A | 2/1989 | Morrison et al. |
| 5,073,484 | A | 12/1991 | Swanson et al. |
| 5,087,575 | A | 2/1992 | Lau |
| 5,238,924 | A | 8/1993 | Smith |
| 5,246,835 | A | 9/1993 | Suzuki et al. |
| 5,403,744 | A | 4/1995 | Zimmerle |
| 5,415,994 | A | 5/1995 | Imrich et al. |
| 5,424,193 | A | 6/1995 | Pronovost et al. |
| 5,656,502 | A | 8/1997 | MacKay et al. |
| 5,723,441 | A | 3/1998 | Higley et al. |
| 6,001,658 | A | 12/1999 | Fredrickson |
| 6,153,392 | A | 11/2000 | Liao et al. |
| 6,190,878 | B1 | 2/2001 | Pierson et al. |
| 6,214,813 | B1 | 4/2001 | Zhang et al. |
| 7,172,873 | B2 | 2/2007 | McDonald et al. |
| 7,482,128 | B2 | 1/2009 | Jensen et al. |
| 2002/0187133 | A1 | 12/2002 | Kubota et al. |
| 2003/0060453 | A1 | 3/2003 | Zhang et al. |
| 2004/0175754 | A1 | 9/2004 | Bar-Or et al. |

FOREIGN PATENT DOCUMENTS

| | | |
|---|---|---|
| EP | 0 198 639 A1 | 10/1986 |
| EP | 0830206 B1 | 1/2001 |
| JP | 04248941 A | 9/1992 |
| JP | 05-302922 | 11/1993 |
| WO | WO 94/01775 | 1/1994 |
| WO | WO 94/29696 | 12/1994 |
| WO | WO 96/40434 | 12/1996 |
| WO | WO 00/37944 | 1/2000 |

OTHER PUBLICATIONS

Bakris, George L., *Curr. Opin. in Neph. and Hypertension*, 1996, vol. 5, pp. 219-223.
Bakris, G.L., *J. Clin. Hypertens (Greenwich)*, 2001, vol. 2, pp. 99-102.
Batamuzi, et al., *Veterinary Record*, 1998, vol. 143, pp. 16-20.
Berrut, et al., *Clinical Nephrology*, 1997, vol. 48, No. 2, pp. 92-97.
German, et al., *Veterinary Immunology and Immunopathology*, 1998, vol. 64, pp. 107-121.
Kilaru, et al., *Journal of Human Hypertension*, 1994, vol. 8, pp. 809-817.
Mogensen, C.E., *Diabetologia*, 1999, vol. 42, pp. 263-285.
Pinto-Sietsma, et al., *J Am Soc Nephrol*, 2000, vol. 11, pp. 1882-1888.
Vaden, *Proc. 17th ACVIM*, 1999, 420.
Viberti, GianCarlo, *American Journal of Hypertension, Ltd.*, 1994, vol. 7, pp.
Watts, *Clin. Chem.*, 1986, vol. 32, No. 8, pp. 1544-1548.
Syme, et al., Proceedings 18th ACVIM, Seattle, WA, May 25-28, 2000, Abstract #97.
Burne, et al., 1998, *Clinical Science*, vol. 95, pp. 67-72.
Comper, et al., Feb. 2003, *American Journal of Kidney Diseases*, vol. 41, No. 2, pp. 336-342.
Osicka, et al., Sep. 2000, *Diabetes*, vol. 49, pp. 1579-1584.
Miller, et al., 1993, *Electrophoresis*, vol. 14, pp. 1312-1317.
Rinsho Kensa Ho Teiyou (General view of clinical test method; the 30th revision), ed. Masamitsu Kanai, Aug. 1993, publisher Kanahara Publishing Col, Ltd., pp. 99-101, see sect. 7, urinary specific gravity, pp. 113-114, section, determination of trace amount of albumin.
Pandjaitan, et cl., 2000, *J. Allergy Clin. Immunol.*, vol. 105 (2 Pt 1), pp. 279-285.
Hilger, et al., 1996, *Gene*, vol. 169, pp. 295-296.
Ho, et al., 1993, *Eur. J. Biochem.*, vol. 215, pp. 205-212.
Boutin et al., "Mapping of cat albumin using monoclonal antibodies: identification of determinants common to cat and dog," Clin. Exp. Immunol., Sep. 1989, vol. 77, pp. 440-444.
Kawanishi et al., "Determinations of Microproteinuria in Early Diabetic Nephropathy," Rinshobyori (Clinical Pathology), 1995, vol. 43, No. 5, pp. 454-459.
Shibasaki et al., "Renal Function," Rinsho to Kenkyu (Clinic and Study), 1995, vol. 72, No. 9, pp. 2132-2135.

(Continued)

*Primary Examiner* — Lisa V Cook
(74) *Attorney, Agent, or Firm* — Sheridan Ross PC

(57) ABSTRACT

The present invention provides a method for the detection of early renal disease in animals. The method includes the steps of (a) obtaining a sample from an animal to be tested and (b) determining the amount of albumin in the sample. An amount of albumin in the range of from 10 µg/ml to about 300 µg/ml indicates the presence of early renal disease. The present invention also provides antibodies to canine, feline and equine albumin which can be used to detect the presence of early renal disease.

20 Claims, No Drawings

OTHER PUBLICATIONS

Ziyadeh et al., "Long-term prevention of renal insufficiency, excess matrix gene expression, and glomerular mesangial matrix expansion by treatment with monoclonal antitransforming growth factor-β antibody in db/db diabetic mice," PNAS, 2000, vol. 97, No. 14, pp. 8015-8020.

International Search Report for International (PCT) Patent Application No. PCT/US02/11105, mailed Sep. 12, 2002.

International Preliminary Examination Report for International (PCT) Patent Application No. PCT/US02/11105, mailed May 19, 2004.

Official Action for Canadian Patent Application No. 2,442,074, dated Nov. 20, 2007.

Official Action for Canadian Patent Application No. 2,442,074, dated Oct. 2, 2008.

Official Action for Canadian Patent Application No. 2,442,074, dated Aug. 26, 2009.

European Search Report for European Patent Application No. 02733963.9, dated Jun. 23, 2004.

Official Action for European Patent Application No. 02733963.9, dated Nov. 26, 2007.

Official Action for European Patent Application No. 02733963.9, dated May 27, 2008.

Official Action for European Patent Application No. 02733963.9, dated Jan. 29, 2009.

Official Action (without translation) for Japanese Patent Application No. 2006-63412, dated Sep. 6, 2007.

Official Action (English translation only) for Japanese Patent Application No. 2006-63412, mailed Jun. 17, 2008.

Official Action (including translation) for Japanese Patent Application No. 2006-63412, Appeal No. 2008-23552, mailed Jan. 18, 2010.

Official Action (including translation) for Japanese Patent Application No. 2008-264647, mailed May 6, 2010.

ized by glomerular changes detectable by histopathology, including the use of light microscopy or occasionally immunofluorescence as reported in Vaden, *Proc. 17<sup>th</sup> ACVIM,* 420 (1999). However, as reported in that paper, these techniques can lead to misdiagnosis of the cause of the renal disease. Determining the cause of the renal disease is useful in

METHODS OF DETECTING EARLY RENAL DISEASE IN ANIMALS

CROSS REFERENCE TO RELATED APPLICATIONS

This application is a divisional of U.S. patent application Ser. No. 10/112,648, filed on Mar. 28, 2002, now U.S. Pat. No. 7,172,873 entitled "METHODS OF DETECTING EARLY RENAL DISEASE IN ANIMALS"; which claims priority to U.S. Provisional Patent Application Ser. No. 60/342,268, filed on Dec. 21, 2001, entitled "METHODS FOR DETECTING EARLY RENAL DISEASE IN ANIMALS"; and U.S. Provisional Patent Application Ser. No. 60/279,391, filed on Mar. 28, 2001, entitled "METHODS FOR DETECTING EARLY RENAL DISEASE IN CANIDS"; all of which are incorporated herein by reference in their entirety.

FIELD OF THE INVENTION

The present invention relates to detection of early renal disease in animals, and more particularly to use of microalbuminuria as a marker of early renal disease.

BACKGROUND OF THE INVENTION

Glomerular disease is a broad term used to describe a number of renal diseases that can lead to renal failure and death. Damage to the glomerulus increases capillary permeability to proteins such as albumin, resulting in the presence of proteins in urine (referred to as proteinuria).

In humans, proteinuria can result from a number of diseases, including diabetes, hypertension and IgA nephropathy. The conventional test for proteinuria in humans is to use a standard protein dipstick assay as described, for example, in Bakris, *Curr. Opin. in Neph. and Hypertension,* 5:219-223 (1996). Dipsticks that are chemically impregnated with sulfosalicylic acid to measure proteins in a sample are commercially available, for example from Boehringer-Mannheim, Germany (CHEMSTRIP®) and Ames Co., USA (AL-BUSTIX®). One drawback to these dipstick assays is that they require a significant amount of protein in the urine to be detected. Amounts of protein in humans of less than 300 milligrams per day are not detectable by the dipstick assay, yet proteinuria may still be present. Another drawback to these protein-based assays is that they are incapable of discriminating between different types of protein (e.g., albumin, globulin, etc.) that may be present in urine. Proteinuria may result from the leakage of serum proteins into glomerular filtrate due to glomerulernephritis; however, proteinuria may also be present due to problems unrelated to renal disease such as bladder infections or a high-protein diet.

Lower amounts of albumin in the urine, referred to as "microalbuminuria," indicate a level of albumin that is greater than in normal patients, but lower than in patients with overt proteinuria, i.e., clinically proteinuric. In humans, microalbuminuria refers to amounts of albumin between 30 milligrams per day and 300 milligrams per day according to Watts, *Clin. Chem.,* 32(8):1544-1548 (1986). Methods to detect human microalbuminuria are known and include those methods that use an anti-human albumin antibody to detect amounts of human albumin that are not detectable by known dipstick methods. Such methods of detecting human microalbuminuria are described, for example, in U.S. Pat. No. 5,246,835, issued on Sep. 21, 1993, to Suzuki et al.

Although microalbuminuria can be detected in humans, the utility of detecting microalbuminuria in humans may be very limited, at least according to some reports. For example, using the microalbuminuria tests to predict renal disease has only been recommended for humans with diabetes according to Bakris, supra. Because disorders other than diabetes, such as hypertension, heart disease and IgA nephropathy do not lead to consistent microalbuminuria in humans, according to Bakris, supra, detecting microalbuminuria has poor predictive value for later renal disease associated with these non-diabetic disorders states. Accordingly, using microalbuminuria tests to screen for potential or early renal disease in non-diabetic human patients is generally not recommended by Bakris, supra.

Renal disease is also a significant health problem in companion animals, particularly dogs and cats. In dogs, the primary cause of renal disease is damage to the glomerulus in the kidney. Although glomerular damage in dogs can occur in any number of ways, it is most commonly caused when circulating immune complexes (i.e., antibody/antigen complexes) are deposited in the glomerular capillaries as a result of systemic illness as described in Batamuzi, et al., *Vet Record,* 143; 16-20 (1988). Several diseases have been implicated in the pathogenesis of immune complex formation, including for example, dirofilariasis and other parasitic infections, diabetes, hypothyroidism and others.

Early renal disease in veterinary medicine has been characterized by glomerular changes detectable by histopathology, including the use of light microscopy or occasionally immunofluorescence as reported in Vaden, *Proc. 17<sup>th</sup> ACVIM,* 420 (1999). However, as reported in that paper, these techniques can lead to misdiagnosis of the cause of the renal disease. Determining the cause of the renal disease is useful in formulating an appropriate treatment regimen. For example, if the cause of the renal disease is immune-mediated, then immunosuppressive therapy may be appropriate. However, currently available assays to detect human microalbuminuria are not sufficiently sensitive to detect canine microalbuminuria.

Thus, a need exists for assays to detect canine early renal disease in companion animals. The present invention satisfies this need and provides related advantages as well.

SUMMARY OF THE INVENTION

The present invention relates to a method and kit for the detection of early renal disease in animals. Preferred animals to test for early renal disease are companion animals with dogs, cats and horses being the most preferred. Method and kit embodiments disclosed herein are based on the discovery that the presence of albumin in a sample from an animal, in the range of 10 µg/ml to 300 µg/ml can be used as an indicator of early renal disease. The most preferred sample to test is urine although any sample that is useful for measuring leakage of albumin from the glomerulus can be used. Any assay capable of detecting albumin may be used in the instant method or kit although preferred methods and kits employ immunologically-based assays, preferably single-step assays. The most preferred assay is an immunologically-based assay utilizing an anti-albumin antibody.

The present invention also provides isolated antibodies which can be used in detecting albumin levels in animal samples. Any antibody which binds albumin from the test animal can be used; preferred antibodies bind canine albumin and/or feline albumin and/or equine albumin. Preferred antibodies are TNB1, TNB3, TNB4, TNB5, TNB6, H352, H386, H387, H388, H389, H390, H391, H393, H394, H395, H396, H397, H398, H399, H400, H401, and H402. Also included are cultured cells which produce antibodies suitable for practicing the present invention.

DETAILED DESCRIPTION OF THE INVENTION

The present invention generally relates to a novel method of detecting early renal disease in animals and to novel antibodies that selectively bind to albumin from one or more specie of animal. More particularly, the present invention relates to the discovery that the presence of microalbuminuria can be used to predict early renal disease in animals, particularly immune-mediated renal diseases. Therefore, the methods can also be useful for prescribing a treatment for an animal. Suitable treatment can be designed to delay or prevent the onset of late-stage renal disease. Examples of such treatment include, for example, pharmacological or dietary modification. The present invention is also useful in monitoring the effectiveness of a prescribed treatment.

A method of the present invention can be generally accomplished by:

(a) obtaining a sample from an animal; and
(b) determining the amount of albumin in the sample.

An amount of albumin in a range of from about 10 μg/ml to about 300 μg/ml in the sample is indicative of early renal disease.

It is to be noted that the term "a" entity or "an" entity refers to one or more of that entity. For example, a protein refers to one or more proteins or at least one protein. As such, the terms "a" "an" "one or more" and "at least one" can be used interchangeably herein. The terms "comprising," "including," and "having" can also be used interchangeably. In addition, the terms "amount" and "level" are also interchangeable and may be used to describe a concentration or a specific quantity. Furthermore, the term "selected from the group consisting of" refers to one or more members of the group in the list that follows, including mixtures (i.e. combinations) of two or more members.

As used herein, the term "renal disease" is defined as a dysfunction of the glomerular filtration process. Glomerular dysfunction may be transient or it may be chronic, depending on the underlying cause of the disease. One consequence of glomerular dysfunction is that proteins which are normally retained in the blood, leak through the glomerulus, into the glomerular filtrate and eventually into the urine. One example of a protein which may be present in urine due to glomerular dysfunction is albumin and its presence in urine at low levels has been termed microalbuminuria. The term "microalbuminuria," as used herein, refers to an amount of albumin that is present in a sample in a range from about 10 μg/ml to about 300 μg/ml when the sample is normalized to a specific gravity of 1.010. This is greater than the amount found in healthy animals which is typically low, i.e., less than 10 μg/ml. Microalbuminuria may arise as a consequence of damage to the kidney resulting from, for example, immune-complex-mediated glomerulemephritis. As used herein, the term "late-stage renal disease" is used to define a state in which an animal has lost 70% or more of its renal function, with corresponding, elevated levels in the animal's serum metabolites, in particular blood-urea nitrogen (BUN) and serum creatinine levels. As used herein, the term "early renal disease" is defined as the presence of microalbuminuria in an animal in the absence of detectable changes in renal function (i.e. increased BUN, serum creatinine or decreased ability to concentrate urine). As such, an albumin level in a sample ranging from about 10 μg/ml to about 300 μg/ml when the sample is normalized to a specific gravity of 1.010 is indicative of early renal disease.

As used herein, the term "animal" is meant to encompass any non-human organism capable of developing early renal disease. Suitable animals to test for microalbuminuria include, but are not limited to companion animals (i.e. pets), food animals, work animals, or zoo animals. Preferred animals include, but are not limited to, cats, dogs, horses, ferrets and other Mustelids, cattle, sheep, swine, and rodents. More preferred animals include cats, dogs, horses and other companion animals, with cats, dogs and horses being even more preferred. As used herein, the term "companion animal" refers to any animal which a human regards as a pet. As used herein, a cat refers to any member of the cat family (i.e., Felidae), including domestic cats, wild cats and zoo cats. Examples of cats include, but are not limited to, domestic cats, lions, tigers, leopards, panthers, cougars, bobcats, lynx, jaguars, cheetahs, and servals. A preferred cat is a domestic cat. As used herein, a dog refers to any member of the family Canidae, including, but not limited to, domestic dogs, wild dogs, foxes, wolves, jackals, and coyotes and other members of the family Canidae. A preferred dog is a domestic dog. As used herein, a horse refers to any member of the family Equidae. An equid is a hoofed mammal and includes, but is not limited to, domestic horses and wild horses, such as, horses, asses, donkeys, and zebras. Preferred horses include domestic horses, including race horses.

In one embodiment of the present invention, a sample is obtained, or collected, from an animal to be tested for microalbuminuria. The animal may or may not be suspected of having early stage renal disease. A sample is any specimen obtained from the animal that can be used to measure albumin leakage from the glomerulus. A preferred sample is a bodily fluid that can be used to measure albumin leakage from the glomerulus. Those skilled in the art can readily identify appropriate samples.

Urine is particularly suitable as the sample. Urine samples can be collected from animals by methods known in the art, including, for example, collecting while the animal is voiding, or collecting by catheterization, or by cystocentesis. Urine may be refrigerated or frozen before assay, but is preferably assayed soon after collection.

Although not necessary for the present invention, the sample may be pre-treated as desired. For example, the sample can be normalized to a desired specific gravity. Normalizing the sample by appropriate dilution methods known in the art permits quantification of microalbuminuria independent of the concentration (e.g. specific gravity) of the sample. Although any desired specific gravity can be readily selected by those skilled in the art, a particularly suitable specific gravity is 1.010. If another specific gravity value is desired for normalizing a sample, those skilled in the art can readily determine the appropriate albumin amounts that would fall within the definition of microalbuminuria for the desired specific gravity.

After obtaining the sample, the level of albumin in that sample is determined. As used herein, the terms "determine," "determine the level of albumin," "determine the amount of albumin," "determine the albumin level," and the like are meant to encompass any technique which can be used to detect or measure the presence of albumin in a sample. Albumin is an example of an analyte. The term "analyte, as used herein, is used to describe any molecule or compound present in a sample. Such techniques may give qualitative or quantitative results. Albumin levels can be determined by detecting the entire albumin protein or by detecting fragments, degradation products or reaction products of albumin. In a preferred method, the level of albumin is determined using a suitable albumin-binding compound.

As used herein, the terms "albumin-binding molecule", "albumin-binding compound", "anti-albumin compound", and the like are used interchangeably and refer to any molecule which binds to albumin and forms a stable complex. A preferred albumin-binding compound is one which selectively binds albumin from an animal. The term "selectively binds albumin" means to preferentially bind to albumin as opposed to binding other proteins unrelated to albumin. A particularly useful albumin-binding compound is a anti-albumin antibody. As used herein, the terms "anti-albumin antibody," "antibody to albumin," "antibody to animal albumin," "antibody having specificity for albumin from animals," "animal albumin antibody," and the like refer to an antibody that preferentially binds albumin from one or more animals. A particularly suitable anti-albumin antibody preferentially binds to canine, feline and/or equine albumin as opposed to binding to different, unrelated canine, feline or equine proteins. Another particularly suitable anti-albumin antibody preferentially binds to canine albumin as opposed to binding to a different, unrelated canine protein. Another particularly suitable antibody to companion animal albumin preferentially binds to feline albumin as opposed to binding to a different, unrelated feline protein. Another particularly suitable antibody to companion animal albumin preferentially binds to equine albumin as opposed to binding to a different, unrelated equine protein.

The present invention also includes isolated (i.e., removed from their natural milieu) antibodies that selectively bind to albumin of one ore more animal species. Isolated antibodies of the present invention can include antibodies in serum, or antibodies that have been purified to varying degrees. Antibodies of the present invention can be polyclonal or monoclonal, or can be functional equivalents such as antibody fragments and genetically-engineered antibodies, including single chain antibodies or chimeric antibodies that can bind to one or more epitopes on albumin. A suitable method to produce antibodies effective for use in the present invention includes (a) administering to an animal an effective amount of a protein, peptide or mimetope thereof to produce the antibodies and (b) recovering the antibodies. Antibodies raised against defined proteins or mimetopes can be advantageous because such antibodies are not substantially contaminated with antibodies against other substances that might otherwise cause interference in a diagnostic assay. Methods to produce such antibodies are known in the art and are described in detail in Harlow et al., *Antibodies, a Laboratory Manual* (Cold Spring Harbor Labs Press, 1988), incorporated by reference herein in its entirety, and include immunizing animals to produce preparations of polyclonal antibodies that are recovered from, for example, ascites fluid and purified by methods known in the art to yield preparations that are reactive to animal albumin. Many species have proteins sharing closely related sequences and therefore it may be difficult using standard immunization protocols to produce antibodies which recognize a protein from only one specie. Therefore, modification of standard methods used to produce antibodies, such as, for example, subtractive hybridization techniques, are also contemplated. Such modifications can be those known to those skilled in the art or additionally modified techniques as disclosed within this application. In another method, antibodies for use in the present invention are produced recombinantly using techniques disclosed in Sambrook et al., *Molecular Cloning: A Laboratory Manual*, (Cold Spring Harbor Labs Press, 1989), incorporated by reference herein in its entirety.

As noted previously, other suitable methods include producing monoclonal antibodies. Briefly, monoclonal antibodies are produced from the fusion of spleen cells from an immunized animal and myeloma cells to produce a hybridoma. Hybridomas can be screened for production of the proper antibody, then cultured and the antibodies harvested. As used herein, the term "cultured cell" refers to hybridomas or any cell which produces an antibody. Methods to produce and screen such hybridomas are described in Harlow, et al., supra. Methods to prepare an antigen so that antibodies produced will be reactive with animal albumin are known in the art and are described, for example, in Harlow, et al., supra. Preparation of the antigen material for injection into the animal includes any technique known in the art, and include, for example, using the full-length protein, using peptides selected from immunogenic regions of the protein, modifying the antigen by methods such as, for example, dinitrophenol coupling, arsynyl coupling, denaturation of the antigen, coupling antigen to protein carriers such as, for example, keyhole limpet hemacyanin, peptides containing Class II-T-cell receptor binding sites, to beads, and any other method known in the art. See Harlow, et al., supra.

The anti-albumin antibodies of the present invention can include multifunctional antibodies, for example a bifunctional antibody having at least one functional portion that specifically binds to animal albumin. Such multifunctional antibodies can include, for example, a chimeric molecule comprising a portion of the molecule that binds to animal albumin and a second portion that enables the chimeric molecule to be bound to a substrate or to be detected in such a manner that the binding to the albumin is unimpaired. Examples of suitable second portions include but are not limited to a fragment of an immunoglobulin molecule, a fluorescent protein or an enzyme.

In addition to anti-albumin antibodies, albumin-binding molecules can also include proteins and peptides that bind to albumin. Such proteins and peptides may be from natural, recombinant or synthetic sources and may or may not be purified. Examples of non-antibody, albumin-binding, proteins include, but are not limited to, the 42-kilodalton (kDa) Protein A from *Staphlococcus aureus*, Protein G from *S. aureus* and *Eschericia coli*, the rat 60-kDa albumin binding protein (gp60) and the human renal tubule cubilin protein. The use of functional homologues of such proteins, from these or other species, for the detection of albumin is also contemplated. Hybrids or fusions of albumin-binding proteins which retain their albumin-binding ability may also be used. In such hybrids, the albumin-binding portion of the protein would be joined to a second portion which allows the hybrid to be bound to a substrate or to be detected. Examples of suitable second portions include, but are not limited to, a fragment of an immunoglobulin molecule, an epitope tag, a fluorescent protein or an enzyme.

An albumin-binding molecule used in the present invention can be contained in a formulation. For example, an antibody can be combined with a buffer in which the antibody is solubilized, and/or with a carrier. Suitable buffers and carriers are known to those skilled in the art. Examples of suitable buffers include any buffer in which an albumin-binding molecule can function to selectively bind to albumin, such as, but not limited to, phosphate buffered saline, water, saline, phosphate buffer, HEPES buffer (N-2-hydroxyethylpiperazine-N'-2-ethansulfonic acid buffered saline) TES buffer (Tris-EDTA buffered saline), Tris buffer and TAE buffer (Trisacetate-EDTA). Examples of carriers include, but are not limited to, polymeric matrices, toxoids, and serum albumins, such as bovine serum albumin. Carriers can be combined with an albumin-binding molecule or conjugated (i.e. attached) to an albumin-binding molecule in such a manner as to not substantially interfere with the ability of the albumin-binding molecule to selectively bind to albumin. In addition, suitable formulations of the present invention can include not only the albumin-binding molecule to specie-specific albumin, but also one or more additional antigens or antibodies useful for detecting albumin.

As used herein, the term "contacting" refers to the introduction of a sample putatively containing albumin to an albumin-binding compound, for example, by combining or mixing the sample with the albumin-binding compound. When albumin is present in the sample, an albumin-compound complex is then formed; such complex formation refers to the ability of an anti-albumin compound to selectively bind to the albumin in order to form a stable complex that can be detected. Detection can be qualitative, quantitative, or semi-quantitative. Binding albumin in the sample to the albumin-binding compound is accomplished under conditions suitable to form a complex. Such conditions (e.g., appropriate concentrations, buffers, temperatures, reaction times) as well as methods to optimize such conditions are known to those skilled in the art. Binding can be measured using a variety of methods standard in the art including, but not limited to, enzyme immunoassays (e.g., ELISA), immunoprecipitations, immunoblot assays and other immunoassays as described, for example, in Sambrook et al., supra, and Harlow, et al., supra. These references also provide examples of complex formation conditions.

In one embodiment, an albumin/albumin-binding compound complex, also referred to herein as an albumin-compound complex, can be formed in solution. In another embodiment, an albumin/albumin-binding compound complex can be formed in which the albumin or the albumin-binding compound is immobilized on (e.g., coated onto) a substrate. Immobilization techniques are known to those skilled in the art. Suitable substrate materials include, but are not limited to, plastic, glass, gel, celluloid, fabric, paper, and particulate materials. Examples of substrate materials include, but are not limited to, latex, polystyrene, nylon, nitrocellulose, agarose, cotton, PVDF (polyvinylidene-fluoride), and magnetic resin. Suitable shapes for substrate material include, but are not limited to, a well (e.g., microtiter dish well), a microtiter plate, a dipstick, a strip, a bead, a lateral flow apparatus, a membrane, a filter, a tube, a dish, a celluloid-type matrix, a magnetic particle, and other particulates. Particularly preferred substrates include, for example, an ELISA plate, a dipstick, an immunodot strip, a radioimmunoassay plate, an agarose bead, a plastic bead, a latex bead, a sponge, a cotton thread, a plastic chip, an immunoblot membrane, an immunoblot paper and a flow-through membrane. In one embodiment, a substrate, such as a particulate, can include a detectable marker. For descriptions of examples of substrate materials, see, for example, Kemeny, D. M. (1991) *A Practical Guide to ELISA*, Pergamon Press, Elmsford, N.Y. pp 33-44, and Price, C. and Newman, D. eds. *Principles and Practice of Immunoassay*, $2^{nd}$ edition (1997) Stockton Press, NY, N.Y., both of which are incorporated herein by reference in their entirety.

In a preferred embodiment, an anti-albumin compound is immobilized on a substrate, such as a microtiter dish well, a dipstick, an immunodot strip, or a lateral flow apparatus. A sample collected from an animal is applied to the substrate and incubated under conditions suitable (i.e., sufficient) to allow for anti-albumin compound-albumin complex formation bound to the substrate (i.e., albumin in the sample binds to the anti-albumin compound immobilized on the substrate).

In accordance with the present invention, once formed, an albumin-binding molecule/albumin complex is detected. As used herein, the term "detecting complex formation" refers to identifying the presence of albumin-binding compound complexed to albumin. If complexes are formed, the amount of complexes formed can, but need not be, quantified. Complex formation, or selective binding, between a putative albumin-composition with an albumin-binding compound can be measured (i.e., detected, determined) using a variety of methods standard in the art (see, for example, Sambrook et al. supra.), examples of which are disclosed herein. A complex can be detected in a variety of ways including, but not limited to use of one or more of the following assays: an enzyme-linked immunoassay, a competitive enzyme-linked immunoassay, a radioimmunoassay, a fluorescence immunoassay, a chemiluminescent assay, a lateral flow assay, a flow-through assay, an agglutination assay, a particulate-based assay (e.g., using particulates such as, but not limited to, magnetic particles or plastic polymers, such as latex or polystyrene beads), an immunoprecipitation assay, a BIACORE® assay (e.g., using colloidal gold), an immunodot assay (e.g., CMG's Immunodot System, Fribourg, Switzerland), and an immunoblot assay (e.g., a western blot), an phosphorescence assay, a flow-through assay, a chromatography assay, a PAGe-based assay, a surface plasmon resonance assay, a spectrophotometric assay, a particulate-based assay, and an electronic sensory assay. Such assays are well known to those skilled in the art.

Assays can be used to give qualitative or quantitative results depending on how they are used. The assay results can be based on detecting the entire albumin molecule or fragments, degradation products or reaction products of albumin. Some assays, such as agglutination, particulate separation, and immunoprecipitation, can be observed visually (e.g., either by eye or by a machines, such as a densitometer or spectrophotometer) without the need for a detectable marker.

In other assays, conjugation (i.e., attachment) of a detectable marker to the anti-albumin compound or to a reagent that selectively binds to the anti-albumin compound aids in detecting complex formation. A detectable marker can be conjugated to the anti-albumin compound or reagent at a site that does not interfere with ability of the anti-albumin compound to bind albumin. Methods of conjugation are known to those of skill in the art. Examples of detectable markers include, but are not limited to, a radioactive label, a fluorescent label, a chemiluminescent label, a chromophoric label, an enzyme label, a phosphorescent label, an electronic label; a metal sol label, a colored bead, a physical label, or a ligand. A ligand refers to a molecule that binds selectively to another molecule. Preferred detectable markers include, but are not limited to, fluorescein, a radioisotope, a phosphatase (e.g., alkaline phosphatase), biotin, avidin, a peroxidase (e.g., horseradish peroxidase), beta-galactosidase, and biotin-related compounds or avidin-related compounds (e.g., streptavidin or IMMUNOPURE® NeutrAvidin).

In one embodiment, an animal albumin-compound complex can be detected by contacting a sample with a specific compound-antibody conjugated to a detectable marker. A detectable marker can be conjugated to an anti-albumin antibody or other compound which binds the albumin-binding-compound in such a manner as not to block the ability of the anti-compound antibody or other compound to bind to the canine albumin-binding compound being detected. Preferred detectable markers include, but are not limited to, fluorescein, a radioisotope, a phosphatase (e.g., alkaline phosphatase), biotin, avidin, a peroxidase (e.g., horseradish peroxidase), beta-galactosidase, and biotin-related compounds or avidin-related compounds (e.g., streptavidin or IMMUNOPURE® NeutrAvidin).

In another embodiment, a complex is detected by contacting the complex with an indicator molecule. Suitable indicator molecules include molecules that can bind to the albumin/albumin-binding molecule complex or to the albumin. As such, an indicator molecule can comprise, for example, an albumin-binding reagent, such as an antibody. Preferred indicator molecules that are antibodies include, for example, antibodies reactive with the antibodies from species of animal in which the anti-albumin antibodies are produced. An indicator molecule itself can be attached to a detectable marker of the present invention. For example, an antibody can be conjugated to biotin, horseradish peroxidase, alkaline phosphatase or fluorescein.

The present invention can further comprise one or more layers and/or types of secondary molecules or other binding molecules capable of detecting the presence of an indicator molecule. For example, an untagged (i.e., not conjugated to a detectable marker) secondary antibody that selectively binds to an indicator molecule can be bound to a tagged (i.e., conjugated to a detectable marker) tertiary antibody that selectively binds to the secondary antibody. Suitable secondary antibodies, tertiary antibodies and other secondary or tertiary molecules can be readily selected by those skilled in the art. Preferred tertiary molecules can also be selected by those skilled in the art based upon the characteristics of the secondary molecule. The same strategy can be applied for subsequent layers.

Preferably, the indicator molecule is conjugated to a detectable marker. A developing agent is added, if required, and the substrate is submitted to a detection device for analysis. In some protocols, washing steps are added after one or both complex formation steps in order to remove excess reagents. If such steps are used, they involve conditions known to those skilled in the art such that excess reagents are removed but the complex is retained.

One embodiment to detect microalbuminuria involves the use of a lateral flow assay, examples of which are described in U.S. Pat. No. 5,424,193, issued Jun. 13, 1995, by Pronovost et al.; U.S. Pat. No. 5,415,994, issued May 16, 1995, by Imrich et al; WO 94/29696, published Dec. 22, 1994, by Miller et al.; and WO 94/01775, published Jan. 20, 1994, by Pawlak et al.; all of which are incorporated by reference herein. A lateral flow assay is an example of a single-step assay. In a single-step assay, once the sample has been obtained and made ready for testing, only a single action is necessary on the part of the user to detect the present of an analyte. For example, the sample, in whole or part, can be applied to a device which then measures analyte in the sample. In one embodiment, a sample is placed in a lateral flow apparatus that includes the following components: (a) a support structure defining a flow path; (b) a labeling reagent comprising a bead conjugated to a specific antibody, the labeling reagent being impregnated within the support structure in a labeling zone; and (c) a capture reagent. Preferred antibodies include those disclosed herein. The capture reagent is located downstream of the labeling reagent within a capture zone fluidly connected to the labeling zone in such a manner that the labeling reagent can flow from the labeling zone into the capture zone. The support structure comprises a material that does not impede the flow of the beads from the labeling zone to the capture zone. Suitable materials for use as a support structure include ionic (i.e., anionic or cationic) material. Examples of such a material include, but are not limited to, nitrocellulose, PVDF, or carboxymethylcellulose. The support structure defines a flow path that is lateral and is divided into zones, namely a labeling zone and a capture zone. The apparatus can further include a sample receiving zone located along the flow path, preferably upstream of the labeling reagent. The flow path in the support structure is created by contacting a portion of the support structure downstream of the capture zone, preferably at the end of the flow path, to an absorbent capable of absorbing excess liquid from the labeling and capture zones.

In another embodiment, a lateral flow apparatus used to detect albumin includes: (a) a support structure defining a flow path; (b) a labeling reagent comprising a anti-albumin antibody as described above, the labeling reagent impregnated within the support structure in a labeling zone; and (c) a capture reagent, the capture reagent being located downstream of the labeling reagent within a capture zone fluidly connected to the labeling zone in such a manner that the labeling reagent can flow from the labeling zone into the capture zone. The apparatus preferably also includes a sample receiving zone located along the flow path, preferably upstream of the labeling reagent. The apparatus preferably also includes an absorbent located at the end of the flow path. One preferred embodiment includes a capture reagent comprising anti-canine albumin antibody.

Once the albumin level has been measured, an assessment of whether early renal disease is present can then be made. Assessing the presence of early renal disease means comparing the level of albumin in the test sample to the level found in healthy animals. The presence of microalbuminuria in the sample, in the absence of changes in renal function, is indicative of early renal disease. As used herein, the term "indicative of early renal disease" is means sufficient glomerular dysfunction is present to allow albumin to pass into the urine in the range of from about 10 µg/ml to about 300 µg/ml. The amount of albumin present in the sample may vary depending on the amount of damage present but in early renal disease, the albumin level is higher than that found in healthy animals but lower than that detectable by current methods used to measure proteinuria. In the present invention, a determination of early renal disease is made when the level of albumin in the sample is determined to be in the range of from about 10 µg/ml to about 300 µg/ml. The upper range of albumin levels can also be about 25 µg/ml, about 50 µg/ml, about 75 µg/ml, about 100 µg/ml, about 125 µg/ml, about 150 µg/ml, about 175 µg/ml, about 200 µg/ml, about 225 µg/ml, about 250 µg/ml, about 275 µg/ml, or about 300 µg/ml. The level of albumin in the sample may vary depending on the severity of the damage to the kidney. Preferred embodiments of the present inventions can detect albumin when about 10%, about 20%, about 30%, about 40%, about 50%, about 60%, about 70%, about 80%, or about 90% of kidney function is lost. A more preferred embodiment can detect microalbuminuria in time for medical intervention which may then delay or prevent the onset of late-stage renal disease. Such intervention may, for example, include, but is not limited to the use of pharmacological compounds or dietary modifications to delay or prevent the progression of renal disease.

One embodiment of the present invention is a "dipstick" device which can detect microalbuminuria in animals. Dipsticks may be constructed in a variety of ways that partly depend on the way in which they will be used. They may be held directly in a sample (e.g., a urine stream), dipped directly in sample contained in a collection vessel, or have sample applied to a strip contained in a plastic cassette or platform. Another example of a dipstick is a "flow-through" device, an example of which is a heterogenous immunometric assay system based on a capture antibody immobilized onto a membrane attached to an absorbent reservoir, A "bead" refers to a particulate substrate composed of a matrix such as latex or polystyrene, which can be covalently or non-covalently cross-linked to a detection molecule. A preferred embodiment of the "dipstick" assay is an immunometric system, described in U.S. Pat. No. 5,656,502, issued on Aug. 12, 1997, to MacKay and Fredrickson, and U.S. Pat. No. 6,001,658, issued Dec. 14, 1999 to Fredrickson, both incorporated herein by reference. Particularly preferred is an IMMUNODIP® device available from Diagnostic Chemicals Ltd., PEI, CA.

Non-immunological methods may also be used. In order to detect microalbuminuria, methods such as preconcentration of the urine in order to concentrate albumin may be used to increase sensitivity of the test to protein. Such non-immunological methods include, for example, urine electrophoresis, where detection of microalbuminuria can be determined by methods known in the art, and include, for example, protein staining. In another embodiment, a protein based albumin test may be used to determine microalbuminuria on a preconcentrated sample of urine from an animal.

The methods of the present invention can be used to detect nephropathy in a canid, felid, equid, or other animal, particularly when the nephropathy is glomerulonephropathy, and especially glomerulonephritis. More specifically, the microalbuminuria measurement is correlated to the presence of early renal disease in a target animal. As used herein, the term "nephropathy" and/or "renal disease" refers to any disease of the kidneys, and may include, for example, nephritis of the glomerular, tubular, or interstitial renal tissues.

Such early stage nephropathy can result from many different causes, including, for example, allergy, cancer, parasitic, viral, or bacterial infection of any tissue in the animal, exposure to renal toxins, immune-mediated diseases, such as systemic lupus eythematosus and vasculitis, malignancy, Vitamin D3 rodenticides, pyelonephritis, leptospirosis, urinary tract obstruction, chronic inflammatory disease, pyoderma, pancreatitis, prostatitis, immune-mediated diseases, dental disease, high blood pressure, or diabetes. As used herein, an "infectious agent" is one that infects animals and include, but are not limited to, viruses, bacteria, fungi, endoparasites and ectoparasites. Examples of viral infectious agents include, but are not limited to, adenoviruses, caliciviruses, coronaviruses, distemper viruses, hepatitis viruses, herpesviruses, immunodeficiency viruses, infectious peritonitis viruses, leukemia viruses, oncogenic viruses, papilloma viruses, parainfluenza viruses, parvoviruses, rabies viruses, and reoviruses, as well as other cancer-causing or cancer-related viruses. Examples of bacterial infectious agents include, but are not limited to, *Actinomyces, Bacillus, Bacteroides, Bartonella, Bordetella, Borrelia, Brucella, Campylobacter, Capnocytophaga, Clostridium, Corynebacterium, Coxiella, Dermatophilus, Ehrlichia, Enterococcus, Escherichia, Francisella, Fusobacterium, Haemobartonella, Helicobacter, Klebsiella*, L-form bacteria, *Leptospira, Listeria, Mycobacteria, Mycoplasma, Neorickettsia, Nocardia, Pasteurella, Peptococcus, Peptostreptococcus, Proteus, Pseudomonas, Rickettsia, Rochalimaea, Salmonella, Shigella, Staphylococcus, Streptococcus*, and *Yersinia*. Examples of fungal infectious agents include, but are not limited to, *Absidia, Acremonium, Alternaria, Aspergillus, Basidiobolus, Bipolaris, Blastomyces, Candida, Chlamydia, Coccidioides, Conidiobolus, Cryptococcus, Curvalaria, Epidermophyton, Exophiala, Geotrichum, Histoplasma, Madurella, Malassezia, Microsporum, Moniliella, Mortierella, Mucor, Paecilomyces, Penicillium, Phialemonium, Phialophora, Prototheca, Pseudallescheria, Pseudomicrodochium, Pythium, Rhinosporidium, Rhizopus, Scolecobasidium, Sporothrix, Stemphylium, Trichophyton, Trichosporon*, and *Xylohypha*. Examples of protozoan parasite infectious agents include, but are not limited to, *Babesia, Balantidium, Besnoitia, Cryptosporidium, Eimeria, Encephalitozoon, Entamoeba, Giardia, Hammondia, Hepatozoon, Isospora, Leishmania, Microsporidia, Neospora, Nosema, Pentatrichomonas, Plasmodium, Pneumocystis, Sarcocystis, Schistosoma, Theileria, Toxoplasma*, and *Trypanosoma*. Examples of helminth parasite infectious agents include, but are not limited to, *Acanthocheilonema, Aelurostrongylus, Ancylostoma, Angiostrongylus, Ascaris, Brugia, Bunostomum, Capillaria, Chabertia, Cooperia, Crenosoma, Dictyocaulus, Dioctophyme, Dipetalonema, Diphyllobothrium, Diplydium, Dirofilaria, Dracunculus, Enterobius, Filaroides, Haemonchus, Lagochilascaris, Loa, Mansonella, Muellerius, Nanophyetus, Necator, Nematodirus, Oesophagostomum, Onchocerca, Opisthorchis, Ostertagia, Parafilaria, Paragonimus, Parascaris, Physaloptera, Protostrongylus, Setaria, Spirocerca, Spirometra, Stephanofilaria, Strongyloides, Strongylus, Thelazia, Toxascaris, Toxocara, Trichinella, Trichostrongylus, Trichuris, Uncinaria*, and *Wuchereria*. Examples of ectoparasite infectious agents include, but are not limited to, fleas, ticks, including hard ticks and soft ticks, flies such as midges, mosquitoes, sand flies, black flies, horse flies, horn flies, deer flies, tsetse flies, stable flies, myiasis-causing flies and biting gnats, ants, spiders, lice, mites, and true bugs, such as bed bugs and kissing bugs.

The present invention may also be used to measure multiple analytes. Other analytes may be any analyte which can be detected in sample suitable for use in detecting early renal disease. Additional analytes can be used to detect, for example, infectious disease or inborn errors of metabolism.

The present invention also relates to antibodies that bind to albumin from an animal being tested. A preferred antibody is one which detects albumin levels when the amount in the sample is about 50 µg/ml, more preferably 25 µg/ml, more preferably 10 µg/ml. Another preferred antibody is one which detects albumin levels when the amount in the sample is about 50 µg/ml, more preferably about 25 µg/ml, more preferably about 10 µg/ml and the detection method is a dipstick device described in U.S. Pat. No. 6,001,658. A preferred antibody is one which competes with any of the monoclonal antibodies TNB1, TNB3, TNB4, TNB5, TNB6, H352, H386, H387, H388, H389, H390, H391, H393, H394, H395, H396, H397, H398, H399, H400, H401, or H402 for selective binding to animal albumin, preferably canine albumin. Another preferred embodiment is an antibody which binds to the same or related epitope, as defined by sequence homology, bound by the antibodies TNB3, TNB6 and H402. A preferred antibody is selected from the group consisting of TNB1, TNB3, TNB4, TNB5, TNB6, H352, H386, H387, H388, H389, H390, H391, H393, H394, H395, H396, H397, H398, H399, H400, H401, and H402. More preferred is an antibody selected from the group consisting of TNB3, TNB6 and H402. As used herein, the terms "compete" and "inhibit selective binding" refer to the ability of an antibody to prevent another antibody from binding to the same protein as described in the included examples.

The present invention also includes kits suitable for detecting animal albumin using the methods disclosed herein. Suitable means of detection include the techniques disclosed herein, utilizing compounds that bind the desired animal albumin, such as, for example, an anti-albumin antibody. As such, a kit can also comprise a detectable marker, such as an antibody that selectively binds to the albumin binding compound or other indicator molecules. The kit can also contain associated components, such as, but not limited to, buffers, labels, containers, inserts, tubings, vials, syringes and the like.

The present invention is based on a surprising discovery that microalbuminuria in canids can be used as a marker to predict the development of renal disease in nondiabetic dogs as well as diabetic dogs because microalburninuria does not clearly have predictive value in nondiabetic human patients. Similar uses are contemplated in other animals. However, despite this surprising discovery, until the present invention, effective methods to detect microalbuminuria in dogs did not exist. Conventional human microalbuminuria detection methods do not detect dog microalbuminuria as described in the examples below.

The following examples are provided for the purposes of illustration and are not intended to limit the scope of the present invention.

Example 1

Measurement of Microalbuminuria in Normal, CRF and ARF Dogs

Urine samples were collected from 134 canine patients at the Colorado State University Teaching Hospital. These samples included urine from normal dogs, dogs suffering chronic renal failure, dogs suffering acute renal failure, and proteinuric dogs without renal failure. Samples were frozen at −20° C. for at least 24 hours and then thawed prior to use. Albumin levels were quantified by a microradial immunodiffision assay as described in McDonald, Weber & Thiele, "Construction and Use of a Template Block for Radial Immunodiffusion" *Anal Biochem* 186:165-168 (1990) using a commercial anti-albumin antibody (polyclonal rabbit anti-dog albumin, available from Nordic Immunology distributed by Accurate Chemical and Scientific Corp., Westbury, N.Y.). For this assay the antibody at 1.5% (vol/vol) was added to melted 0.75% (wt/vol) EEO agarose in PBS. Gels, at a thickness of 0.75 mm were poured between two glass plates. The gels were allowed to solidify and after one of the glass plates was removed, allowed to dry slightly. Acrylic blocks, described in McDonald et al., supra., were placed on the agarose and 5 μl sample or standard was placed in each well of the acrylic block. Samples were run either undiluted or if the resulting ring was too large to measure the sample was diluted and re-tested. The standard curve using dog albumin (dog albumin fraction V, available from Sigma, St. Louis, Mo.) was linear within the range of 10-100 μg/ml. The acrylic blocks were left on the agarose and the unit was placed in a moist chamber and incubated overnight at room temperature. The agarose gels were then soaked in distilled water for several hours to remove the excess protein from the gel, the gel was dried and then stained with Coomassie Brilliant Blue so that the precipitin rings could be readily visualized. The diameter of each ring was measured and the ring diameter from each sample was compared to the standard curve and the albumin concentration of each sample was calculated.

The advantage of using this system for measuring albumin in the urine is that this system is more sensitive that the traditional assay with wells cut into the gels. This increased sensitivity is related to the to the concentrated delivery of the antigen into a small area as opposed to the larger surface area created by the edges of a well cut into the agarose For this initial study, samples that had less than or equal to 50 μg/ml were deemed normal, samples that had levels between 51 and 300 μg/ml were deemed microalbuminuric, and those that had levels over 300 μg/ml were deemed macroalbuminuric. The results of this study are shown in Table 1.

TABLE 1

Urinary albumin levels in 134 canine urine samples

| Albumin Level | Number of Animals | Percentage |
| --- | --- | --- |
| Normal (0-50 μg/ml) | 59 | 44% |
| Microalbuminuria (51-300 μg/ml) | 21 | 16% |
| Macroalbuminuria (>300 μg/ml) | 54 | 40% |

Example 2

ELISA Quantification of Microalbuminuria

Rabbit anti-canine serum albumin IgG (anti-CSA IgG) is diluted to 375 ng/ml in coating buffer (50 mM $Na_2CO_2$/$NaCHO_3$, pH 9.6). The diluted anti-CSA IgG solution is added to a plate of MAXISORP™ C8 Break-apart Microwells (Nunc Cat. #473768) at 100 μl/well, covered and incubated overnight (16 to 24 hours) at 4° C. The plate is washed four times with phosphate buffered saline with 0.05% Tween 20 (PBS-T) in an automatic plate washer and blotted dry. Blocking buffer (STABILCOAT® available from Surmodics Cat. #SC01-1000) is added at 200 μl/well, covered and incubated at room temperature for at least 1 hour.

While blocking, the canine serum albumin (CSA) dilution series is prepared. First, the CSA is diluted to 120 ng/ml in assay diluent (0.1% casein hydrolysate in PBS-T). This solution is serially diluted (1 part to 1 part) to make 66 ng/ml, 30 ng/ml, 7.5 ng/ml, 3.75 ng/ml, and 1.875 ng/ml. The last 5 standards are used for the standard curve (30 ng/ml and less) along with a "zero" standard (assay diluent with no CSA). Each urine sample to be tested is diluted 11500, 1/1000, 1/2000, 1/4000, 1/8000, 1/16000 and 1/32000 in assay diluent.

The plate is then washed four times in an automatic plate washer and blotted dry. The CSA standard and diluted urine sample are added at 100 μl/well of each to the test wells. Assay diluent is added to duplicate wells for background control. The plate is covered and incubated for 2 hours at room temperature. As previously, the plate is washed four times with PBS-T and blot dry.

Dilute biotin labeled goat anti-CSA IgG (Bethyl Laboratories, Cat. #E40-113)] to 125 ng/ml in assay diluent. Add 100 μl/well of diluted biotin labeled goat anti-CSA IgG to all test wells. Cover plate and incubate for 30 minutes at room temperature. As previously, wash the plate four times with PBS-T and blot dry.

Dilute horseradish peroxidase labeled streptavidin (KPL Cat. # 14-30-00) to 500 ng/ml (1/1000 dilution) in assay diluent and add to all test wells at 100 μl/well. Cover and incubate at room temperature for 30 minutes. As previously, wash the plate four times with PBS-T and blot dry.

Mix TMB microwell peroxidase 2 component system (KPL Cat. #50-76-03) solutions together at equal volumes and add 100 μl/well of the TMB mixture to all wells. Cover and incubate for 30 minutes at room temperature. The reaction is stopped by adding 100 μl/well of stop solution (1M $H_3PO_4$) directly to the TMB in each well. Read the wells at 450 nm in a spectrophotometer. Average the values of all duplicate wells, if any, and subtract background value from all the test values. Generate a standard curve from the standard values and generate a regression line ($r^2$>0.95). Using the regression formula, compute the CSA (ng/ml) value for each sample and multiply this value by the dilution factor. Only those values that fall in the linear portion of the standard curve should be used.

Example 3

Use of the IMMUNODIP® stick for the Detection of Microalbuminuria in Canine Urine Three IMMUNODIP® sticks (product number 700-01) for the detection of microalbuminuria in humans, were obtained from Diagnostic Chemicals Limited, Charlottetown, Prince Edward Island, Canada. Two canine urine samples (numbered 1086 and 1098) were selected from a group of samples obtained from dogs at the Colorado State University Veterinary Teaching Hospital, Fort Collins, Colo., Samples 1086 and 1098 were selected based on their albumin-levels as determined by an in-house ELISA to detect microalbuminuria in dogs. Sample 1086 was a negative sample, and sample 1098 had an albumin concentration of 221 µg/ml. For a positive control, approximately 50 µl of human blood was added to 5 ml deionized water Measurement of albumin in the urine was performed following the manufacturer's directions. Briefly, 3 ml of urine or the blood-spiked water was added to a test tube. The IMMUNODIP® stick was removed from the pouch and placed in the test tube containing the urine making sure the fluid level was above the vent hole in the device. The device was left in the sample for a minimum of 3 minutes after which it was removed and read by comparing the relative intensities of the two bands according to the interpretation-of-results insert that accompanies the test kit. The results of the in-house ELISA and the IMMUNODIP® tests are shown in Table 2.

TABLE 2

IMMUNODIP ® stick for microalbuminuria results

| Sample | In-House ELISA | IMMUNODIP ® |
|---|---|---|
| 1086 | 0 µg/ml | Negative |
| 1098 | 221 µg/ml | Negative |
| Blood-spiked Water | Not-tested | Positive |

The limit of detection in the IMMUNODIP® test for human urine albumin is 12 µg/ml. Sample 1098 contained canine urine at a level significantly above this lower limit yet was negative for albumin by the IMMUNODIP® test. These data suggest that this device does not recognize canine albumin, at least not in order to detect microalbuminuria.

Example 4

Use of MICRAL® Test Strips for the Detection of Microalbuminuria in Canine Urine Fourteen MICRAL® urine test strips product number 417146) for the detection of microalbuminuria in humans, were obtained from Roche BMC, Indianapolis, Ind. Thirteen canine urine samples were selected from a group of samples obtained from employee's dogs. Samples for use were selected based on their albumin-levels as determined by an in-house ELISA to detect microalbuminuria in dogs. Samples 2A, 4A & 16 A were negative samples while the remaining samples had albumin concentrations ranging in value from 31.3 to >650 µg/ml. As a positive control, 50 µl of human blood was added to 5 ml deionized water.

Measurement of albumin in the urine was performed following the manufacturer's directions. Briefly, each dog's urine was collected in a sample collection cup. In addition, blood-spiked water was placed in a test tube. The MICRAL® stick was removed from the vial and placed in the collection cup (or test tube containing the blood-spiked water) making sure the fluid level was above the devices two black lines in each case. The device was left in sample for 5 seconds, removed and allowed to sit horizontally for 1 minute. The result was determined by comparing the color of the test pad to the color scale on the vial in accordance with the result insert that accompanied the test. The results of the in-house ELISA and the MICRAL® test are shown in Table 3.

The detection limit in the MICRAL® test for human albumin is about 20 µg/ml. Several samples contained canine albumin levels significantly above this lower limit yet were negative for albumin by the MICRAL® test. These data suggest that this device does not recognize canine urine albumin, at least not in order to detect microalbuminuria.

TABLE 3

MICRAL ® urine test strip results

| Sample | In-house ELISA | MICRAL ® |
|---|---|---|
| 1A | 79.4 µg/ml | Negative |
| 2A | 3.9 µg/ml | Negative |
| 4A | 5.9 µg/ml | Negative |
| 5A | 35.9 µg/ml | Negative |
| 9A | 48.6 µg/ml | Negative |
| 15A | 69.4 µg/ml | Negative |
| 16A | 8.3 µg/ml | Negative |
| 29A | 119.1 µg/ml | Negative |
| 86A | 31.3 µg/ml | Negative |
| 87A | 65.2 µg/ml | Negative |
| 14 | >650 µg/ml | Negative |
| 19 | Positive | Negative |
| 45 | 650 µg/ml | Negative |
| Blood-spiked water | Not tested | Positive |

Example 5

Use of the IMMUNODIP® stick for the Detection of Microalbuminuria in Canine Urine Fourteen IMMUNODIP® sticks product number 700-01) for the detection of microalbuminuria in humans, were obtained from Diagnostic Chemicals Limited, Charlottetown, PE, Canada. Thirteen canine urine samples were selected from a group of samples obtained from dogs that were apparently normal. Samples for use were selected based on their albumin levels as determined by an in-house ELISA to detect microalbuminuria in dogs. Samples 2A, 4A & 16 A were negative samples while the remaining samples had albumin concentrations ranging in value from 31.3 to >650 µg/ml. As a positive control, 50 µl of human blood was added to 5 ml deionized water.

Measurement of albumin in the urine was performed following the manufacturer's directions. Briefly, 3 ml of urine or the blood-spiked water was added to a test tube. The IMMUNODIP® stick was removed from the pouch and placed in the test tube containing the urine making sure the fluid level was above the device's vent hole in each case. The device was left in the sample for a minimum of 3 minutes after which, it was removed and read by comparing the relative intensities of the two bands according to the interpretation-of-results insert that accompanies the test kit. The results of the in-house ELISA and the IMMUNODIP® tests are shown in Table 4.

TABLE 4

IMMUNODIP ® Stick for Microalbuminuria results

| Sample | In-house ELISA | IMMUNODIP ® |
|---|---|---|
| 1A | 79.4 µg/ml | Negative |
| 2A | 3.9 µg/ml | Negative |
| 4A | 5.9 µg/ml | Negative |
| 5A | 35.9 µg/ml | Negative |
| 9A | 48.6 µg/ml | Negative |
| 15A | 69.4 µg/ml | Negative |
| 16A | 8.3 µg/ml | Negative |
| 29A | 119.1 µg/ml | Negative |
| 86A | 31.3 µg/ml | Negative |
| 87A | 65.2 µg/ml | Negative |
| 14 | >650 µg/ml | Negative |
| 19 | Positive | Negative |
| 45 | 650 µg/ml | Negative |
| Blood-spiked water | Not tested | Positive |

The detection limit in the IMMUNODIP® test for human albumin is about 20 µg/ml. Several samples contained canine albumin levels significantly above this lower limit yet were negative for albumin by the IMMUNODIP® test. These data suggest that this device does not recognize canine urine albumin, at least not in order to detect microalbuminuria.

Example 6

Use of MICRAL® Test Strips for the Detection of Microalbuminuria in Canine Urine Five MICRAL® urine test strips (product number 417146) for the detection of microalbuminuria in humans were obtained from Roche BMC, Indianapolis, Ind. Thirteen canine urine samples were selected from a group of samples obtained from dogs that were apparently normal. Samples for use were selected based on their albumin-levels as determined by an in-house ELISA to detect microalbuminuria in dogs. Samples 7 and 12 were negative samples while samples 14 and 25 had albumin levels of 621 µg/ml and >650 µg/ml, respectively. As a positive control, 50 µl of human blood was added to 5 ml deionized water.

Measurement of albumin in the urine was performed following the manufacturer's directions. Briefly, each dog's urine was collected in a sample collection cup. For the positive control, blood-spiked water was placed in a test tube. The MICRAL® stick was removed from the vial and placed in the collection cup (or test tube containing the blood-spiked water) making sure the fluid level was above the devices two black lines in each case. The device was left in sample for 5 seconds, removed and allowed to sit horizontally for 1 minute. The result was determined by comparing the color of the test pad to the color scale on the vial in accordance with the result insert that accompanied the test. The results of the in-house ELISA and the MICRAL® test are shown in Table 5.

TABLE 5

MICRAL ® urine test strip results

| Sample | In-House ELISA | MICRAL ® |
|---|---|---|
| 7 | 2.1 µg/ml | Negative |
| 12 | 0.8 µg/ml | Negative |
| 14 | 621 µg/ml | Negative |
| 25 | >650 µg/ml | Negative |
| Blood-spiked water | Not tested | Positive |

The limit of detection in the MICRAL® test for human urine albumin is about 20 µg/ml. Samples 14 and 25 contained canine albumin levels significantly above these lower levels yet were negative for albumin by the MICRAL® test. These data suggest that this device does recognize canine urine albumin, at least not in order to detect microalbuminuria.

Example 7

Prevalence of Microalbuminuria in Dogs

For this study, two separate populations were examined. One sample population was derived from clinically normal dogs (n=86). The second sample population was derived from Colorado State University Teaching Hospital patients (n=150) presented for routine health screening, elective procedures, as well as evaluation of health problems. Microalbuminuria was quantitated using an antigen capture ELISA. The results of this measurement were normalized to a specific gravity of 1.010 to account for varying urine concentrations. Albumin in the urine of the hospital patients was also tested using PETSTIX™ 8 urine protein test strips (Idexx Cat. #98-06959-00).

Of the 86 clinically normal dogs, 68 (79%) had normalized albumin concentrations<1.0 mg/dL, 16 (19%) had normalized albumin concentrations>1.0 mg/dL and <30.0 mg/dL, and 2 (2%) had normalized albumin concentrations>30.0 mg/dL. Of the 159 hospital patients, 112 (70%) were urine test strip negative and 51 of the 112 (46%) test-strip negative samples had normalized albumin concentrations>1.0 mg/dL. Conversely, 19 of 80 (24%) of samples with <1.0 mg/Dl albumin were positive on urine test strip (see Table 6).

TABLE 6

| Normalized Urine Albumin Concentrations | Urine Protein Test Strip Result (n = 159) | | | |
|---|---|---|---|---|
| (# of samples) | Neg. (112) | Trace (20) | 1+ (15) | 2-4+ (12) |
| <1.0 mg/dL (80) | 61 (54%) | 12 (60%) | 5 (33%) | 2 (17%) |
| >1.0 and <30.0 mg/dL (58) | 49 (44%) | 6 (30%) | 2 (13%) | 1 (8%) |
| >30.0 mg/dL (21) | 2 (2%) | 2 (10%) | 8 (53%) | 9 (75%) |

In the two populations examined, prevalence of microalbuminuria (>1.0 mg/dL and <30.0 mg/dL) ranged from 19% to 36%. From these results, it appears microalbuminuria is prevalent in a significant number of dogs. Furthermore, use of commercially available urine protein test strips for the detection of albuminuria yields a substantial number of false positive results.

Example 8

Purification of Canine Serum Albumin

This Example discloses a method for producing canine serum albumin. Canine serum was adjusted to 50% (w/v) ammonium sulfate, the solution rocked for 3 hours at 4° C., and the insoluble material precipitated by centrifugation at 10,000×g for 30 minutes. The supernatant was removed and dialyzed into 25 mM Tris, pH 8.0. The soluble material was loaded onto a pre-equilibrated, Hi-Trap Q-Sepharose column (Pharmacia, Peapack, N.J.) and the proteins eluted using a linear gradient of 0 to 1.0 M NaCl over 25 column volumes (CV). Collected fractions were analyzed by SDS-PAGe and fractions containing canine albumin were pooled and stored until needed. Using this method, 414 mg of albumin was purified from 20 ml of canine serum. Protein sequencing confirmed the purified protein was canine albumin.

Example 9

Production of Anti-Canine Albumin Antibodies

This example discloses the method used to produce monoclonal antibodies (Mabs) TNB1, TNB2, TNB3, TNB4, TNB5, TNB6 which recognize canine serum albumin (CSA). Balb/C mice were immunized by subcutaneous injection with Complete Freunds Adjuvant mixed with either 25 µg, 50 µg or 100 µg of canine serum albumin (available from Sigma, St. Louis, Mo.). After four weeks, blood samples were obtained and anti-CSA antibody titers determined by ELISA. Based on this data, the three mice immunized with 100 µg of CSA were chosen for further use in producing hybridomas. Two of these mice were given intravenous (IV) injections containing 100 µg of CSA and the third mouse received 100 µg intraperitoneally. Three days later, the mice were euthanized, the spleens removed and depleted of T-cells and the spleen cells fused with SP2/0 mouse myeloma cells following standard protocols. Individual hybridoma colonies were tested for the production of MAbs which recognize CSA and positive colonies were expanded and dilution cloned until stable MAb secreting lines were established.

Example 10

Production of Anti-Canine Albumin Antibodies using Subtractive Hybridization

This Example discloses procedures utilizing subtractive hybridization techniques to produce monoclonal antibodies (Mabs) which recognize canine serum albumin (CSA).

Anti-canine CSA hybridoma cell lines were produced using the following, published method of subtractive hybridization. Balb/C mice were injected intraperitoneally with 1.0 mg of BSA Fraction V (available from Boehringer Manheim, Indianapolis, Ind.), followed by IP injections of cyclophosphamide (CY)(100 mg/kg) at 10 minutes, 24, and 48 hours post-BSA injection. This BSA/CY treatment was repeated two weeks later. After another two weeks, the mouse was given a subcutaneous (SC) injection containing 100 µg of CSA (produced as described in Example 8) mixed with Complete Freunds Adjuvant. After an additional two weeks had passed, blood samples were obtained and serum antibody titers against CSA and BSA were determined by ELISA. A second injection of CSA (100 µg) was then given intraperitoneally to boost the animals anti-CSA antibody titers. Two weeks later, the mouse was given an intravenous (IV) injection of CSA (50 µg) and after three days, the mouse was sacrificed, its splenocytes harvested and fused with mouse SP2/0 myeloma cells using polyethylene glycol (PEG) following standard procedures. Individual hybridoma colonies were tested for the production of MAbs which recognize CSA and positive colonies were expanded and dilution cloned until stable MAb secreting lines were established. This procedure resulted in the production of hybridoma lines H398 and H399.

In addition to the hybridoma cells lines produced by the above procedure, the following modified subtractive hybridization procedure was used to produce additional anti-CSA hybridoma cell lines. 30 µg of CSA (produced as described in Example 8) were injected into the footpad of a Balb/C mouse. Three months later, the mouse was given an intraperitoneal (IP) injection containing 30 µg of CSA. Four months after the IP injection, the mouse was given a second IP injection containing 1.0 mg of BSA, followed by IP injections of cyclophosphamide (CY)(100 mg/kg) at 10 minutes, 24, and 48 hours post-BSA injection. After two weeks, this BSA/CY treatment was repeated and after two more weeks had elapsed, the mouse was given a subcutaneous (SC) injection of CSA (100 µg) mixed with complete Freunds adjuvant. After another two weeks, blood samples were obtained and serum antibody titers against CSA and BSA were determined by ELISA. The mouse was then given an intravenous (IV) injection of CSA (50 µg) and three days later, the mouse was euthanized, its splenocytes harvested and fused with mouse SP2/0 myeloma cells using polyethylene glycol (PEG) following standard procedures. Individual hybridoma colonies were tested for the production of MAbs which recognize CSA and positive colonies were expanded and dilution cloned until stable MAb secreting lines were established. This protocol resulted in the production of hybridoma cell lines H384, H385, H386, H387, H388, H389, H390, H391, H392, H393, H394, H395, H396, H400, H401 and H402.

Example 11

Detection of Canine Serum Albumin by ELISA

This example discloses the use of a solid-phase ELISA to test the ability of the anti-canine serum albumin (CSA) antibodies to detect CSA.

The wells of a microtiter plate were coated with CSA (50 µg/well) (produced as described in Example 8) in carbonate buffer (50 mM carbonate/bicarbonate, pH 9.6) and the plate stored overnight at 4° C. The following day, excess liquid was removed, the plate blotted dry, and 150 µl of Blocking buffer (0.1% casein in PBS containing 0.05% Tween-20) were added to each well. The plate was incubated at room temperature (RT) for 30 minutes, after which, the Blocking buffer was removed and 50 µl of hybridoma supernatant (either undiluted or diluted in blocking buffer) were added to each well. Following a one hour incubation at RT, the wells were washed twice using Wash buffer (PBS containing 0.05% Tween-20), 50 µl of HRP-conjugated, goat, anti-mouse IgG and IgM (available from KPL Labs, Gaithersburg, Md.) were added to each well and the plate incubated at RT for 30 minutes. The wells were washed twice with Wash buffer, and 50 µl of TMB Substrate System (available from KPL Labs) were added to each well. The plate was incubated at RT for 10 minutes after which, the reaction was stopped by the addition of 50 µl of 2N sulfuric acid to each well. The plate was read at 450 nM using an ELISA plate reader and the results are shown below in Table 7.

TABLE 7

| Antibody | Undiluted | 1:10 | 1:100 |
| --- | --- | --- | --- |
| TNB1 | 1288 | 852 | 326 |
| TNB3 | 1242 | 1263 | 922 |
| TNB4 | 1449 | 1431 | 1546 |
| TNB5 | 1528 | 1585 | 1478 |
| TNB6 | 1782 | 1436 | 1103 |
| H386 | 1274 | 1273 | 1187 |
| H387 | 1394 | 1369 | 1326 |
| H388 | 1485 | 1529 | 1408 |
| H389 | 1685 | 1646 | 1265 |
| H390 | 1558 | 892 | 250 |
| H391 | 1490 | 1325 | 916 |
| H393 | 1744 | 1603 | 1640 |
| H394 | 435 | 955 | 577 |
| H395 | 1265 | 1049 | 1001 |

TABLE 7-continued

| Antibody | Undiluted | 1:10 | 1:100 |
|---|---|---|---|
| H396 | 1564 | 1773 | 1390 |
| H397 | 49 | 59 | 48 |
| H398 | 1822 | 1641 | 1501 |
| H399 | 775 | 144 | 64 |
| H400 | 1572 | 1610 | 1239 |
| H401 | 1839 | 1683 | 1511 |
| H402 | 1799 | 1752 | 1447 |

Example 12

Detection of Albumin from Several Species by ELISA

This example demonstrates the ability of three anti-canine albumin monoclonal Abs to recognize bovine (BSA), canine (CSA), equine (HSA) or human (HuSA) serum albumin by ELISA using the protocol outlined in Example 11 with the exception the wells were coated with 3× serial dilutions (from 5 μg/ml to 0.002 g/ml) of the indicated albumin. In addition, 10 μg of the indicated antibody was used in each well. The results are shown in Table 8.

TABLE 8

| Albumin Concentration (μg/ml) | Coat Protein | | | |
|---|---|---|---|---|
| | BSA | CSA | HSA | HuSA |
| TNB3 | | | | |
| 5 | .62 | 3.53 | 1.67 | .12 |
| 1.667 | .52 | 3.50 | 1.37 | .15 |
| .556 | .43 | 3.51 | .87 | .17 |
| .185 | .57 | 3.43 | .34 | .16 |
| .062 | .20 | 3.14 | .19 | .15 |
| .021 | .17 | 2.08 | .16 | .16 |
| .007 | .17 | .35 | .13 | .13 |
| .002 | .11 | .20 | .09 | .10 |
| TNB6 | | | | |
| 5 | .18 | 3.68 | .90 | 1.69 |
| 1.667 | .42 | 3.59 | .69 | .78 |
| .556 | .30 | 3.59 | .52 | .47 |
| .185 | .24 | 3.43 | .32 | .23 |
| .062 | .22 | 3.17 | .26 | .26 |
| .021 | .21 | 2.36 | .22 | .22 |
| .007 | .20 | 1.18 | .21 | .22 |
| .002 | .22 | .55 | .21 | .23 |
| H402 | | | | |
| 5 | .41 | 3.41 | .87 | .97 |
| 1.667 | .40 | 3.35 | .71 | .59 |
| .556 | .38 | 3.31 | .57 | .41 |
| .185 | .35 | 3.23 | .42 | .37 |
| .062 | .32 | 2.98 | .36 | .34 |
| .021 | .35 | 2.10 | .32 | .31 |
| .007 | .35 | 1.20 | .18 | .31 |
| .002 | .35 | .65 | .32 | .33 |

This data demonstrates mAb's TNB3, TNB6 and H402 have a much greater affinity for CSA as compared with BSA, HSA or HuSA.

Example 13

Competition ELISA using the anti-albumin mAb's H402, TNB3 and TNB6

This example compares the ability of the H402, TNB3 and TNB6 monoclonal antibodies to compete for binding to canine serum albumin (CSA). Competition between antibodies was measured by coating an entire ELISA plate with CSA, adding a labeled primary antibody to all the wells of the plate and then measuring the ability of several unlabeled antibodies to compete with the primary antibody for binding to the CSA. (All primary antibodies were labeled using biotin available from Pierce Chemical, Rockford, Ill. according to the manufacturers instructions). In this manner, each plate was used to test the ability of a single primary antibody to compete with two other anti-albumin antibodies for the ability to bind CSA. In addition, antibody raised against the extracellular domain of human high affinity IgE receptor alpha chain (anti-FcϵRIα) was used on each plate as a negative control. The details of the assay are as follows:

Three ELISA plates were coated overnight at 4° C. with CSA at 1 μg/ml. The following day, the wells were washed using Wash buffer (PBS+0.05% Tween-20) and blocked with Blocking Solution (STABILCOAT® IMMUNOASSAY STABILIZER; available from SurModics, Inc., Eden Prairie, Minn.) according to the manufacturer's directions. The wells were then washed using Wash buffer, and 100 μl of a single, labeled, primary antibody, either H402 at 20 ng/ml, TNB3 at 8 ng/ml or TNB6 at 12 ng/ml (concentrations were adjusted using Dilution buffer (0.1% casein in PBS+0.05% Tween-20)) were added to all of the wells of an individual plate so that each plate held a different primary antibody. To one row of wells on each plate was then added 100 μl of unlabeled secondary antibody, either H402, TNB3, TNB6 or anti-HuFCϵR1 at 20 μg/ml. Two-fold serial dilutions were then performed, diluting each secondary antibody across the plate so that the final concentrations of secondary antibody were from 10 ug/ml to 9 ng/ml. The plates were incubated at room temperature (RT) for 2 hours, washed with Wash buffer and 100 μl of horse-radish-peroxidase conjugated Streptavidin (diluted 1:1000 in Dilution buffer) were added. Following a 1 hour incubation at RT, the wells were washed with Wash buffer and 100 μl of developing solution (TMB Substrate; available from KPL Labs, Gaithersburg, Md.) were added to each well. After a 30 minute RT incubation, the plates were read at 450 nm using an ELISA plate reader. The results of this assay are shown below in Table 9.

TABLE 9

| Antibody Concentration (ng/ml) | Competing (secondary) Antibody | | | |
|---|---|---|---|---|
| | H402 | TNB3 | TNB6 | Anti-HuFCER1 |
| H402 as Primary Antibody | | | | |
| 10000 | .069 | 2.292 | .087 | 2.584 |
| 5000 | 0.164 | 2.328 | 0.195 | 2.576 |
| 2500 | 0.271 | 2.341 | 0.300 | 2.551 |
| 1250 | 0.517 | 2.275 | 0.559 | 2.569 |
| 625 | 1.212 | 2.255 | 1.093 | 2.592 |
| 312.5 | 2.104 | 2.262 | 1.683 | 2.540 |
| 156.25 | 2.548 | 2.293 | 2.239 | 2.557 |
| 78.125 | 2.670 | 2.381 | 2.402 | 2.512 |
| 39.06 | 2.752 | 2.461 | 2.514 | 2.518 |
| 19.53 | 2.765 | 2.427 | 2.655 | 2.660 |
| 9.77 | 2.798 | 2.657 | 2.611 | 2.639 |
| 0 | 2.710 | 2.641 | 2.577 | 2.642 |
| TNB3 as Primary Antibody | | | | |
| 10000 | 2.295 | 0.090 | 2.290 | 2.479 |
| 5000 | 2.493 | 0.245 | 2.409 | 2.645 |
| 2500 | 2.445 | 0.395 | 2.247 | 2.508 |
| 1250 | 2.480 | 0.796 | 2.185 | 2.397 |
| 625 | 2.485 | 1.534 | 2.239 | 2.428 |
| 312.5 | 2.378 | 2.084 | 2.208 | 2.483 |

TABLE 9-continued

| Antibody Concentration (ng/ml) | Competing (secondary) Antibody | | | |
|---|---|---|---|---|
| | H402 | TNB3 | TNB6 | Anti-HuFCER1 |
| 156.25 | 2.529 | 2.535 | 2.324 | 2.484 |
| 78.125 | 2.463 | 2.643 | 2.351 | 2.497 |
| 39.06 | 2.566 | 2.674 | 2.390 | 2.509 |
| 19.53 | 2.607 | 2.740 | 2.520 | 2.602 |
| 9.77 | 2.763 | 2.716 | 2.611 | 2.669 |
| 0 | 2.867 | 2.798 | 2.756 | 2.764 |
| TNB6 as Primary Antibody | | | | |
| 10000 | 0.122 | 2.307 | 0.134 | 2.490 |
| 5000 | 0.303 | 2.410 | 0.310 | 2.604 |
| 2500 | 0.459 | 2.177 | 0.473 | 2.569 |
| 1250 | 0.769 | 2.276 | 0.733 | 2.550 |
| 625 | 1.446 | 2.283 | 1.383 | 2.501 |
| 312.5 | 2.126 | 2.319 | 2.053 | 2.402 |
| 156.25 | 2.502 | 2.430 | 2.358 | 2.564 |
| 78.125 | 2.647 | 2.455 | 2.480 | 2.516 |
| 39.06 | 2.743 | 2.496 | 2.557 | 2.530 |
| 19.53 | 2.745 | 2.579 | 2.605 | 2.582 |
| 9.77 | 2.787 | 2.697 | 2.654 | 2.559 |
| 0 | 2.772 | 2.685 | 2.319 | 2.377 |

The data demonstrate that the monoclonal antibodies H402 and TNB6 compete for binding of canine serum albumin consistent with these antibodies sharing the same, or closely related, epitopes. The data further demonstrate that binding of canine serum albumin by TNB3 is unaffected by H402 or TNB6.

Example 14

Binding of Canine and Feline Albumin by H352, H398 and TNB3

This example compares the ability of three anti-albumin antibodies (H352, H398 & TNB3) to bind canine (CSA) or feline (FSA) albumin.

The binding assay was performed as follows. To enable detection, horse-radish peroxidase (HRP) (Pierce Chemical, Rockford, Ill.) was conjugated to either CSA or ESA following manufacturer's protocol. The wells of a microtiter plate were coated with a range (from 10 μg/ml to 9.77 ng/ml) of antibody (either H352, H398 or TNB3) in carbonate buffer (50 mM carbonate/bicarbonate, pH 9.6) and the plates stored overnight at 4° C. The following day, excess liquid was removed and the wells were blocked using blocking solution (STABILCOAT® IMMUNOASSAY STABILIZER; available from SurModics, Inc., Eden Prairie, Minn.) following manufacturer's instructions. Following removal of the blocking solution, the wells were rinsed using Wash buffer (PBS containing 0.05% Tween-20) and HRP-FSA (diluted 1:400 in carbonate buffer) or HRP-CSA (diluted 1:800 in carbonate buffer) were added to the wells and the plate incubated at room temperature (RT) for 30 minutes. The HRP-albumin conjugate was removed, the wells washed twice using Wash Buffer and 50 μl of TMB Substrate System (available from KPL Labs, Gaithersburg, Md.) were added to each well. The plate was incubated at RT for 10 minutes after which the reaction was stopped by the addition of 50 μl of 2N sulfuric acid to each well. The plate was read at 450 nM using an ELISA plate reader. The results are shown below in Table 10.

TABLE 10

| MAb Concentration (ng/ml) | mAb | | | | | |
|---|---|---|---|---|---|---|
| | H352 | | H398 | | TNB3 | |
| | Coat Protein | | | | | |
| | FSA | CSA | FSA | CSA | FSA | CSA |
| 10000 | 4.200 | 4.184 | 2.984 | 3.887 | 0.055 | 4.191 |
| 5000 | 4.200 | 4.200 | 1.944 | 2.806 | 0.047 | 4.184 |
| 2500 | 4.189 | 4.160 | 1.532 | 2.333 | 0.049 | 4.177 |
| 1250 | 4.127 | 4.200 | 1.187 | 1.941 | 0.099 | 4.186 |
| 625 | 2.740 | 4.084 | 0.493 | 0.769 | 0.043 | 4.178 |
| 312.5 | 1.266 | 2.814 | 0.168 | 0.282 | 0.045 | 3.410 |
| 156.25 | 0.713 | 1.598 | 0.095 | 0.135 | 0.043 | 2.400 |
| 78.13 | 0.324 | 0.859 | 0.078 | 0.090 | 0.042 | 1.109 |
| 39.06 | 0.178 | 0.413 | 0.053 | 0.063 | 0.043 | 0.543 |
| 19.53 | 0.107 | 0.236 | 0.047 | 0.055 | 0.049 | 0.309 |
| 9.77 | 0.077 | 0.132 | 0.050 | 0.051 | 0.059 | 0.191 |
| 0 | 0.044 | 0.048 | 0.048 | 0.061 | 0.049 | 0.048 |

The data monoclonal antibody H352 binds to both FSA and CSA with roughly equal affinity. Monoclonal antibody H398 also recognizes both FSA and CSA although it has greater affinity for CSA. Finally, the data demonstrates that monoclonal antibody TNB3 binds specifically binds to CSA and does not bind FSA.

Example 15

Albumin in Canines Suffering Heartworm-Induced Renal Disease

This example discloses the albumin levels present in the canine *Dirofilaria immitis*-induced nephropathy. In this model, animals are infected with *D. immitis* which results in renal damage due to antigen-antibody-complex induced damage of the glomerulus as described in Grauer, G. F., et. al., *American Journal or Tropical Medicine and Hygiene;* 39(4), 1988, p 380-387. It is known in this model that *D. immitis* antigen appears in the blood approximately seven-months post-infection. For this example, animals were infected with *D. immitis* and urine samples collected monthly by catheterization. It should be noted that in some cases, the process of catheterization can result in elevated albumin levels; as a result, animals were only considered positive for micoalbuminuria when they were found to be microalbuminuric in two consecutive samples. The amount of albumin in each sample was determined using an ELISA assay. The results are shown below in Table 11. Boxes labeled N/A indicate where no sample was available.

TABLE 11

| Months Post Infection | Animal Identifier | | | | | | | | | | | |
|---|---|---|---|---|---|---|---|---|---|---|---|---|
| | HOP (A) | IGH (A) | POR (A) | SSH (A) | XTJ (A) | YOH (A) | AXH (B) | CAH (B) | FVH (B) | GUH (B) | HOH (B) | VIP (B) |
| | 174.9 | 0.2 | 2.3 | 1.9 | 0.3 | 2.9 | 8.0 | 72.6 | 0.3 | 3.7 | 4.2 | 2.1 |
| 1 | 2.1 | 3.8 | 2.4 | 0.3 | N/A | 8.7 | 4.0 | 4.0 | | 3.7 | 0.2 | 0.4 |
| 2 | 33.8 | 2.0 | 9.5 | 2.4 | 29.9 | N/A | 3.3 | 0.2 | 3.0 | 3.3 | 0.9 | 2.6 |
| 4 | 1.3 | 16.4 | 0.3 | 3.0 | 0.3 | 0.3 | 3.7 | 22.7 | 2.5 | 2.3 | 1.8 | 5.4 |

TABLE 11-continued

| Months Post Infection | HOP (A) | IGH (A) | POR (A) | SSH (A) | XTJ (A) | YOH (A) | AXH (B) | CAH (B) | FVH (B) | GUH (B) | HOH (B) | VIP (B) |
|---|---|---|---|---|---|---|---|---|---|---|---|---|
| 5 | 2.2 | 4.2 | N/A | 2.0 | 18.1 | 4.2 | 3.4 | 3.0 | 0.3 | 1.9 | 0.2 | 4.1 |
| 6 | 4.9 | 9.9 | N/A | 2.5 | N/A | 0.3 | 0.2 | 2.6 | 2.7 | 1.5 | 0.4 | 0.4 |
| 7 | 1.4 | 48.1 | 0.3 | 0.3 | 20.7 | 45.6 | 3.9 | 0.3 | 1.9 | 20.7 | 3.3 | 8.1 |
| 8 | 8.4 | N/A | 18.0 | N/A | 60.6 | 16.2 | 3.1 | 4.8 | 6.5 | 2.8 | 8.5 | 15.4 |
| 9 | 26.2 | 2.9 | 4.4 | 0.4 | 46.8 | 16.1 | 6.0 | 0.3 | 24.6 | 3.6 | 0.3 | N/A |
| 10 | N/A | 11.0 | 3.4 | 10.8 | 26.2 | 15.7 | 13.1 | 21.3 | 54.0 | 60.3 | 0.2 | 46.0 |
| 11 | 52.1 | 125.7 | 43.5 | 36.9 | 180.6 | 67.8 | 3.9 | 27.3 | 11.5 | 6.5 | 59.5 | 736. |
| 12 | 58.5 | 16.2 | 22.2 | 52.9 | 51.3 | 54.9 | 6.8 | 76.2 | 23.4 | 5.9 | 97.4 | 167.2 |
| 13 | 113.5 | 56.4 | 25.1 | 8.1 | 132.4 | 112.7 | 14.7 | 30.1 | 327.2 | 13.3 | 65.5 | 132.6 |
| 14 | 134.3 | 60.2 | 132.1 | 16.8 | 123.0 | 82.9 | 66.6 | 65.8 | 500.0 | 5.0 | 285.7 | 69.06.1 |
| 15 | 206.0 | 4.0 | 122.0 | 23.7 | 39.1 | 18.6 | 3.8 | 16.4 | 500.0 | 8.0 | 107.8 | 34.8 |
| 16 | 37.3 | 7.6 | 500.0 | 5.4 | 52.5 | 10.1 | 5.5 | 17.8 | 500.0 | 4.9 | 43.1 | N/A |
| 17 | N/A | 45.2 | N/A | 8.6 | 181.6 | 89.1 | 30.9 | 19.8 | 500.0 | 16.4 | 53.0 | N/A |
| 18 | 18.8 | 112.1 | 211.1 | 5.4 | 70.4 | 26.8 | 10.5 | 14.9 | N/A | 5.4 | 21.3 | N/A |
| 19 | 16.7 | 67.0 | 176.7 | 12.1 | 208.4 | N/A | N/A | 36.3 | N/A | 4.9 | 57.1 | N/A |
| 20 | N/A | N/A | N/A | N/A | 500.0 | N/A | N/A | N/A | N/A | 1.9 | N/A | N/A |
| 21 | N/A | N/A | N/A | N/A | N/A | 37.9 | 9.2 | 41.7 | N/A | 11.0 | 17.1 | N/A |
| 22 | 1.6 | 4.7 | 75.8 | 9.1 | 500.0 | 27.2 | 22.2 | 500.0 | N/A | 3.2 | 46.2 | N/A |
| 23 | 83.2 | 37.6 | 30.3 | 17.5 | 500.0 | 60.3 | 54.3 | 500.0 | N/A | 5.2 | 37.7 | N/A |

The data demonstrate that following infection with *D. immitis*, there is a progressive increase in the level of albumin in the urine. Additionally, most animals became microalbuminuric within 1-2 months following the time of appearance of *D. immitis* antigen in the blood. Microalbuminuria could be detected in all animals by the end of the study.

Example 16

Albumin Levels in Canines Suffering from Hereditary Nephritis

This example compares the level of microalbuminuria (MA) with a commonly used marker for renal disease, the urinary protein/creatinine (UP/C) ratio, over time in animals suffering from hereditary nephritis (HD). In this model, the animals carry a genetic defect which results in the rapid development of renal disease during the course of the animals life as described in Lee, G E, *American Journal of Veterinary Research*, 1999: 60, p 373-383. In this example, urine was periodically collected from a colony of normal dogs and a colony of dogs suffering HD. The amount of albumin in each sample was determined using an ELISA assay. In addition, the urinary protein/creatinine UP/C ratio was determined using veterinary reference lab. By this measurement, renal disease is considered to be present when the UP/C ratio is greater than 1.0. The results of this study are shown below in Table 12.

TABLE 12

| | Animal Identification | | | | | | | | | |
|---|---|---|---|---|---|---|---|---|---|---|
| | Fonzi (control) | | Jake (control) | | Ned (control) | | Oscar (control) | | Pete (control) | |
| Age (weeks) | UP/C Ratio | MA (µg/ml) | UP/C Ratio | MA | UP/C Ratio | MA (µg/ml) | UP/C Ratio | MA (µg/ml) | UP/C Ratio | MA (µg/ml) |
| 8 | 0.1 | 2 | 1.6 | 0 | 0.2 | 5 | 0.6 | 2 | 0.9 | 3 |
| 11 | 0.2 | 2 | 0.7 | 5 | 0.2 | 5 | 0.2 | 8 | 0.3 | 4 |
| 13 | 0.3 | 1 | 0.3 | 0 | 0.2 | 5 | 0.9 | 3 | 0.4 | 2 |
| 15 | 1.0 | 3 | 0.6 | 6 | 0.2 | 5 | 0.3 | 4 | 0.2 | 2 |
| 17 | 0.2 | 1 | 0.2 | 3 | 0.2 | 5 | 0.1 | 3 | 0.2 | 6 |
| 19 | 0.4 | 15 | 0.5 | 4 | 0.2 | 5 | | | 0.1 | 3 |
| 21 | 0.1 | 4 | 1.0 | 7 | 0.2 | 5 | 0.1 | 2 | 0.1 | 1 |
| 23 | 0.3 | 0 | 0.2 | 3 | 0.2 | 5 | 0.2 | 1 | 0.1 | 1 |
| 25 | 0.6 | 1 | 0.1 | 6 | 0.2 | 5 | 0.1 | 1 | 0.1 | 20 |
| 27 | 0.1 | 1 | 0.2 | 6 | 0.2 | 5 | 0.1 | 0 | 0.1 | 6 |
| 30 | 0.1 | 2 | 0.1 | 4 | 0.2 | 5 | 0.1 | 2 | 0.0 | 1 |
| 34 | 0.2 | 220 | 0.1 | 4 | 0.2 | 5 | 0.1 | 1 | 0.1 | 2 |
| 38 | 0.1 | 1 | 0.1 | 2 | 0.2 | 5 | 0.1 | 1 | 0.1 | 4 |

| | Ethan (HN) | | Frasier (HN) | | Greg (HN) | | Ike (HN) | | Lester (HN) | |
|---|---|---|---|---|---|---|---|---|---|---|
| Age (weeks) | UP/C Ratio | MA (µg/ml) | UP/C Ratio | MA (µg/ml) | UP/C Ratio | MA (µg/ml) | UP/C Ratio | MA (µg/ml) | UP/C Ratio | MA (µg/ml) |
| 8 | 0.2 | 4 | 0.1 | 6 | 0.1 | 2 | 1.0 | 6 | 0.8 | 10 |
| 11 | 0.3 | 9 | 0.2 | 4 | 0.1 | 4 | 0.2 | 10 | 0.4 | 8 |
| 13 | 0.6 | 4 | 0.2 | 1 | 0.3 | 2 | 0.2 | 1 | 0.5 | 12 |
| 15 | 0.5 | 8 | 0.3 | 12 | 0.1 | 12 | 0.7 | 7 | 0.3 | 3 |
| 17 | 0.1 | 17 | 0.6 | 358 | 0.2 | 487 | 1.0 | 557 | 0.4 | 7 |
| 19 | 1.0 | 82 | 2.3 | 314 | 0.4 | 2 | 4.4 | 918 | 0.6 | 115 |

TABLE 12-continued

| | | | | | | | | | |
|---|---|---|---|---|---|---|---|---|---|
| 21 | 3.0 | 136 | 1.1 | 30 | 0.2 | 2 | 6.6 | 1574 | 1.0 | 561 |
| 23 | 6.2 | 4954 | 5.1 | 2145 | 0.3 | 71 | 12.5 | 5560 | 3.0 | 615 |
| 25 | 10.1 | 744 | 9.0 | 3000 | 1.6 | 603 | 16.6 | 2920 | 3.7 | 17 |
| 27 | 6.6 | 1179 | 7.3 | 2020 | 3.5 | 1499 | 15.3 | 3904 | 7.0 | 1477 |
| 30 | 15.7 | 2734 | 12.3 | 2696 | 5.7 | 1733 | 16.5 | 2276 | 9.3 | 1679 |
| 34 | 11.6 | 1901 | 12.9 | 2 | 8.2 | 309 | 4.4 | 3608 | 8.7 | 1992 |
| 38 | 6.4 | 3310 | 13.9 | 3597 | 8.8 | 4845 | 8.5 | 4465 | 8.1 | 1919 |

| | Nate (HN) | | Newt (HN) | | Quark (HN) | | Quirt (HN) | | Eddie (HN) | |
|---|---|---|---|---|---|---|---|---|---|---|
| Age (weeks) | UP/C Ratio | MA (µg/ml) | UP/C Ratio | MA (µg/ml) | UP/C Ratio | MA (µg/ml) | UP/C Ratio | MA (µg/ml) | UP/C Ratio | MA (µg/ml) |
| 8 | 0.4 | 6 | 0.2 | 5 | 0.1 | 2 | 0.4 | 1 | 1.6 | 16 |
| 11 | 0.4 | 0 | 0.4 | 0 | 0.1 | 3 | 0.4 | 4 | 0.2 | 10 |
| 13 | 0.4 | 5 | 0.2 | 4 | 0.7 | 11 | 0.2 | 3 | 0.4 | 6 |
| 15 | 0.4 | 2 | 0.1 | 19 | 0.3 | 5 | 0.1 | 1 | 0.3 | 6 |
| 17 | 0.3 | 4 | 1.1 | 116 | 0.4 | 74 | 0.1 | 12 | 0.1 | 5 |
| 19 | 0.6 | 7 | 1.5 | 265 | 0.6 | 232 | 0.2 | 25 | 0.4 | 10 |
| 21 | 0.2 | 52 | 2.4 | 1321 | 2.8 | 620 | 0.6 | 267 | 1.2 | 1063 |
| 23 | 2.1 | 340 | 8.7 | 2665 | 9.2 | 1223 | 3.4 | 543 | 2.8 | 1307 |
| 25 | 2.2 | 622 | 9.6 | 4711 | 8.8 | 1938 | 4.6 | 1208 | 8.7 | 19471 |
| 27 | 3.2 | 483 | 10.1 | 1309 | 7.8 | 2007 | 9.1 | 3054 | 6.9 | 1052 |
| 30 | 5.8 | 1529 | 9.0 | 2989 | 14.1 | 3419 | 9.3 | 2747 | 13.9 | 3188 |
| 34 | 7.3 | 1483 | 8.8 | 1806 | 13.1 | 3055 | 9.9 | 6379 | 10.5 | 4927 |
| 38 | 8.9 | 2955 | 8.1 | 6487 | 12.2 | 3118 | 9.5 | 3044 | 12.7 | 6717 |

| | Felix (HN) | | Fred (HN) | | Gus (HN) | | Neal (HN) | | Norm (HN) | |
|---|---|---|---|---|---|---|---|---|---|---|
| Age (weeks) | UP/C Ratio | MA (µg/ml) | UP/C Ratio | MA (µg/ml) | UP/C Ratio | MA (µg/ml) | UP/C Ratio | MA (µg/ml) | UP/C Ratio | MA (µg/ml) |
| 8 | 0.7 | 1 | 0.3 | 3 | 0.1 | 5 | 0.8 | 0 | 0.3 | 1 |
| 11 | 0.1 | 8 | 0.1 | 12 | 0.1 | 4 | 0.2 | 3 | 0.1 | 1 |
| 13 | 0.1 | 1 | 0.5 | 1 | 0.1 | 22 | 0.4 | 3 | 0.1 | 0 |
| 15 | 0.3 | 5 | 0.6 | 1 | 0.2 | 55 | 0.1 | 2 | 0.5 | 1 |
| 17 | 0.8 | 122 | 0.5 | 6 | 1.7 | 24 | 0.4 | 2 | 0.7 | 4 |
| 19 | 0.3 | 87 | 0.3 | 13 | 2.2 | 77 | 0.6 | 428 | 0.5 | 7 |
| 21 | 0.8 | 903 | 0.8 | 9 | 3.9 | 16 | 0.6 | 210 | 1.3 | 354 |
| 23 | 2.6 | 1679 | 0.6 | 81 | 9.3 | 1565 | 6.6 | 1335 | 5.7 | 1535 |
| 25 | 6.9 | 16170 | 1.9 | 152 | 6.4 | 3950 | 8.4 | 4091 | 9.5 | 3290 |
| 27 | 10.2 | 2452 | 3.5 | 11 | 5.2 | 1263 | 10.1 | 1158 | 5.5 | 798 |
| 30 | 12.0 | 2612 | 8.1 | 1887 | 8.3 | 2648 | 9.2 | 2523 | 6.8 | 2796 |
| 34 | 9.3 | 4146 | 7.1 | 3403 | 8.5 | 4583 | 10.1 | 1767 | 11.5 | 2603 |
| 38 | 10.4 | 6218 | 10.8 | 7141 | 7.9 | 3758 | 10.4 | 2906 | 7.0 | 3403 |

| | Paul (HN) | | Quinn (HN) | | Scooter (HN) | | | | | |
|---|---|---|---|---|---|---|---|---|---|---|
| Age (weeks) | UP/C Ratio | MA (µg/ml) | UP/C Ratio | MA (µg/ml) | UP/C Ratio | MA (µg/ml) | UP/C Ratio | MA (µg/ml) | UP/C Ratio | MA (µg/ml) |
| 8 | 0.6 | 4 | 0.1 | 5 | 1.4 | | | | | |
| 11 | 0.1 | 8 | 0.1 | 1 | 0.2 | 3 | | | | |
| 13 | 0.4 | 1 | 0.2 | 5 | 0.3 | 7 | | | | |
| 15 | 0.2 | 0 | 0.2 | 1 | 0.1 | 21 | | | | |
| 17 | 0.1 | 6 | 0.1 | 3 | 0.3 | 66 | | | | |
| 19 | 0.7 | 6 | 0.6 | 5 | 2.7 | 323 | | | | |
| 21 | 0.1 | 58 | 0.1 | 16 | 4.3 | 20 | | | | |
| 23 | 1.3 | 206 | 0.6 | 29 | 8.8 | 2678 | | | | |
| 25 | 2.0 | 598 | 1.5 | 224 | 11.3 | 2957 | | | | |
| 27 | 4.2 | 674 | 2.1 | 431 | 10.1 | 3864 | | | | |
| 30 | 4.0 | 2650 | 5.4 | 1468 | 11.2 | 2118 | | | | |
| 34 | 5.5 | 0 | 10.0 | 1395 | 12.5 | 5098 | | | | |
| 38 | 6.4 | 4324 | 8.6 | 1624 | 8.4 | 3238 | | | | |

The data demonstrate that there is a progressive increase in microalbuminuria in animals suffering from hereditary nephritis. In addition, in virtually all animals, micoralbuminuria was detected prior to the UP/C ration being greater than 1.0.

Although the invention has been described with reference to the presently preferred embodiments, it should be understood to those skilled in the art that various modifications can be made without departing from the spirit of the invention. Accordingly, the invention is limited only by the following claims.

What is claimed is:

1. A method to detect early renal disease comprising:
   (a) obtaining a sample from an animal;
   (b) applying at least part of the sample to a device capable of detecting albumin in the sample; and
   (c) obtaining a urinary albumin concentration from the device,
   wherein an amount of albumin in a range from about 10 µg/ml to about 300 µg/ml in the sample, when the specific gravity of the sample is normalized to 1.010 g/ml, is indicative of early renal disease.

2. The method of claim 1, wherein the method is repeated at least once to monitor a disease or the effect of a therapy.

3. The method of claim 1, wherein the device measures the amount of albumin in the sample by:
   (a) contacting the sample with an albumin-binding compound to form an albumin-compound complex;
   (b) detecting the albumin-compound complex; and
   (c) assessing the amount of albumin present in the sample from the amount of albumin-compound complex detected.

4. The method of claim 3, wherein the albumin-binding compound is an anti-albumin antibody.

5. The method of claim 4, wherein said antibody inhibits the selective binding of a test antibody selected from the group consisting of TNB1, TNB3, TNB4, TNB5, TN6, H352, H386, H387, H388, H389, H390, H391, H393, H394, H395, H396, H397, H398, H399, H400, H401 and H402 to albumin.

6. The method of claim 4, wherein the antibody binds the same epitope recognized by a test antibody selected from the group consisting of TNB1, TNB3, TNB4, TNB5, TN6, H352, H386, H387, H388, H389, H390, H391, H393, H394, H395, H396, H397, H398, H399, H400, H401 and H402.

7. The method of claim 1, wherein the device detects albumin in the sample using an assay selected from the group consisting of an enzyme-linked immunoassay, a radioimmunoassay, a fluorescence immunoassay, a chemiluminescent assay, a lateral-flow assay, a dipstick assay, an agglutination assay, a particulate-based assay, an immunoprecipitation assay, an immunodot assay, an immunoblot assay, an immunodiffusion assay, a phosphorescence assay, a flow-through assay, a chromatography assay, a PAGe-based assay, an electronic-sensory assay, a surface plasmon resonance assay and a fluorescence correlation spectroscopy assay.

8. The method of claim 1, wherein the animal is selected from the group consisting of canids, felids and equids.

9. The method of claim 1, wherein the sample is pre-treated by adjusting the specific gravity to 1.010 g/ml.

10. A method to identify an animal at risk for developing late-stage renal disease comprising:
    (a) obtaining a sample from an animal;
    (b) applying at least part of the sample to a device capable of detecting albumin in the sample; and
    (c) obtaining a urinary albumin concentration from the device,
    wherein an amount of albumin in a range from about 10 µg/ml to about 300 µg/ml in the sample, when the specific gravity of the sample is normalized to 1.010 g/ml, is indicative of early renal disease.

11. The method of claim 10, wherein the animal is selected from the group consisting of canids, felids and equids.

12. The method of claim 10, wherein the device measures the amount of albumin in the sample by:
    (a) contacting the sample with an albumin-binding compound to form an albumin-compound complex;
    (b) detecting the albumin-compound complex; and
    (c) assessing the amount of albumin present in the sample from the amount of albumin-compound complex detected.

13. The method of claim 12, wherein the albumin-binding compound is an anti-albumin antibody.

14. A method to detect early renal disease comprising
    (a) obtaining a sample of urine from an animal;
    (b) applying at least part of the sample to a device comprising a support structure defining a capillary flow path, the support structure comprising:
       (i) a sample pad for receiving the sample;
       (ii) a labeling area fluidly connected to the sample pad, the labeling area comprising a labeling reagent that comprises an albumin-binding compound conjugated to a detectable marker;
       (iii) a first capture area fluidly connected to the labeling area, the first capture area comprising an immobilized first capture reagent that binds the albumin-binding compound/detectable marker conjugate, wherein the amount of immobilized first capture reagent is sufficient to capture 50% of the conjugate when the concentration of albumin in the sample is less than 10 ug/ml;
       (iv) a second capture area fluidly connected to the first capture area, the second capture area comprising an immobilized second capture reagent for capturing albumin-binding compound/detectable marker conjugate not captured by the first capture regent;
    (c) comparing the amount of detectable marker in the first and second capture areas;
    wherein a greater relative detectable marker intensity in the second capture area as compared to the detectable marker intensity in the first capture area indicates the presence of early renal disease.

15. The method of claim 14, wherein the albumin-binding compound is an antibody that selectively binds albumin.

16. The method of claim 15, wherein the antibody inhibits the selective binding of an antibody selected from the group consisting of TNB1, TNB3, TNB4, TNB5, TN6, H352, H386, H387, H388, H389, H390, H391, H393, H394, H395, H396, H397, H398, H399, H400, H401 and H402.

17. The method of claim 14, wherein the first capture regent comprises a molecule selected from the group consisting of albumin and an antibody that selectively binds albumin.

18. The method of claim 14, wherein the second capture reagent comprises a molecule selected from the group consisting of albumin and an antibody that binds the albumin-binding compound.

19. The method of claim 14, wherein the animal is selected from the group consisting of canids, felids and equids.

20. The method of claim 14, wherein the sample is pre-treated by adjusting the specific gravity to 1.010 g/ml.

* * * * *